United States Patent
Fried et al.

(10) Patent No.: US 11,752,355 B2
(45) Date of Patent: Sep. 12, 2023

(54) ESTIMATING THE TEMPERATURE OF A HOUSING OF A DEVICE

(71) Applicant: Medtronic, Inc., Minneapolis, MN (US)

(72) Inventors: Andrew T. Fried, St. Paul, MN (US); Venkat R. Gaddam, Plymouth, MN (US); Kunal Paralikar, Little Canada, MN (US); Brett Otteson, Minneapolis, MN (US); Yohan Kim, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 283 days.

(21) Appl. No.: 17/085,701

(22) Filed: Oct. 30, 2020

(65) Prior Publication Data

US 2022/0134116 A1    May 5, 2022

(51) Int. Cl.
*H02J 7/00* (2006.01)
*G01K 1/02* (2021.01)
(Continued)

(52) U.S. Cl.
CPC ....... *A61N 1/3787* (2013.01); *A61N 1/36125* (2013.01); *G01K 1/026* (2013.01);
(Continued)

(58) Field of Classification Search
CPC .. A61N 1/3787; A61N 1/36125; G01K 1/026; G01K 7/427; H01M 10/443;
(Continued)

(56) References Cited

U.S. PATENT DOCUMENTS

| 5,897,576 A | 4/1999 | Olson et al. |
| 6,431,748 B1 | 8/2002 | Baratta |

(Continued)

FOREIGN PATENT DOCUMENTS

| CN | 111459212 A | 7/2020 |
| WO | 2013158238 A2 | 10/2013 |

(Continued)

OTHER PUBLICATIONS

Extended Search Report from counterpart European Application No. 21204171.9, dated Mar. 25, 2022, 7 pp.

(Continued)

*Primary Examiner* — Stacy Whitmore
(74) *Attorney, Agent, or Firm* — Shumaker & Sieffert, P.A.

(57) ABSTRACT

Techniques for estimating the temperature of an external portion of a medical device are described. In an example, processing circuitry may determine a temperature sensed by at least one temperature sensor of an internal portion of the device, and determine, based on an algorithm that incorporates the temperature of the internal portion of the device, an estimated temperature of a second portion of the device, wherein the algorithm is representative of an estimated temperature difference between the first portion of the device and the second portion of the device based at least in part on a dynamic transfer function that operates in a time-domain.

20 Claims, 16 Drawing Sheets

(51) Int. Cl.
*H01M 10/44* (2006.01)
*A61N 1/378* (2006.01)
*A61N 1/36* (2006.01)
*A61B 5/00* (2006.01)
*A61M 25/00* (2006.01)

(52) U.S. Cl.
CPC ..... *H01M 10/443* (2013.01); *H02J 7/007192* (2020.01); *A61B 5/686* (2013.01); *A61M 25/00* (2013.01)

(58) Field of Classification Search
CPC . H02J 7/007192; H02J 2310/23; A61B 5/686; A61B 5/6846; A61B 2560/0219; A61B 2560/0266; A61M 25/00; Y02E 60/10
See application file for complete search history.

(56) References Cited

U.S. PATENT DOCUMENTS

| | | | |
|---|---|---|---|
| 6,681,135 | B1 | 1/2004 | Davis et al. |
| 7,167,756 | B1 | 1/2007 | Torgerson et al. |
| 7,952,322 | B2 | 5/2011 | Partovi et al. |
| 8,244,367 | B2 | 8/2012 | Wahlstrand et al. |
| 8,335,569 | B2 | 12/2012 | Aghassian |
| 8,496,646 | B2 | 7/2013 | Kamen et al. |
| 8,554,322 | B2 | 10/2013 | Olson et al. |
| 8,784,364 | B2 | 7/2014 | Kamen et al. |
| 8,901,878 | B2 | 12/2014 | Prutchi et al. |
| 9,176,163 | B2 | 11/2015 | Heath et al. |
| 9,209,634 | B2 | 12/2015 | Cottrill et al. |
| 9,225,190 | B2 | 12/2015 | Labbe et al. |
| 9,227,076 | B2 | 1/2016 | Sharma et al. |
| 9,270,134 | B2 | 2/2016 | Gaddam et al. |
| 9,653,935 | B2 | 5/2017 | Cong et al. |
| 9,851,372 | B2 | 12/2017 | Heath et al. |
| 9,929,584 | B2 | 3/2018 | Aghassian et al. |
| 10,258,804 | B2 | 4/2019 | Scott et al. |
| 10,554,069 | B2 | 2/2020 | Paralikar et al. |
| 10,971,943 | B2 | 4/2021 | Paralikar et al. |
| 11,394,226 | B2 | 7/2022 | Cong et al. |
| 2003/0050557 | A1 | 3/2003 | Susil et al. |
| 2005/0283144 | A1 | 12/2005 | Shiono et al. |
| 2007/0156179 | A1 | 7/2007 | S.E. |
| 2008/0272742 | A1 | 11/2008 | Hart et al. |
| 2010/0217360 | A1 | 8/2010 | Henriksson |
| 2010/0234921 | A1 | 9/2010 | Torgerson et al. |
| 2010/0256710 | A1 | 10/2010 | Dinsmoor et al. |
| 2011/0077720 | A1 | 3/2011 | Torgerson et al. |
| 2013/0193914 | A1 | 8/2013 | Gaddam et al. |
| 2013/0278226 | A1* | 10/2013 | Cong ............... H02J 7/007192 320/150 |
| 2014/0048174 | A1 | 2/2014 | Lanigan et al. |
| 2015/0157869 | A1 | 6/2015 | Torgerson et al. |
| 2016/0187272 | A1 | 6/2016 | Ishii et al. |
| 2017/0083064 | A1* | 3/2017 | Mittal .................... G05B 15/02 |
| 2018/0159361 | A1* | 6/2018 | Cong ........................ G01J 5/07 |
| 2019/0190296 | A1* | 6/2019 | Paralikar ............... A61M 25/00 |
| 2019/0358395 | A1 | 11/2019 | Olson et al. |
| 2020/0136417 | A1* | 4/2020 | Paralikar ................. H02J 50/10 |
| 2021/0119469 | A1* | 4/2021 | Cong ........................ G01J 5/07 |
| 2021/0226471 | A1* | 7/2021 | Paralikar ........... H02J 7/007192 |

FOREIGN PATENT DOCUMENTS

| | | |
|---|---|---|
| WO | 2016172530 A1 | 10/2016 |
| WO | 2017053067 A1 | 3/2017 |

OTHER PUBLICATIONS

U.S. Appl. No. 17/221,465, filed Apr. 2, 2021, by Paralikar et al.
Colombo, "An Integrated Mechatronic Unit to Control Heating Power of an Electronic Diesel Fuel Heater," Proceedings of the IEEE International Symposium on Industrial Electronics, Dubrovnik, Croatia, ISIE 2005, doi:10.1109/ISIE.2005.1528926, Jun. 20-23, 2005, 6 pp.
Response to Extended Search Report dated Mar. 25, 2022, from counterpart European Application No. 21204171.9, filed Oct. 26, 2022, 20 pp.

* cited by examiner

ESTIMATING THE TEMPERATURE OF A HOUSING OF A DEVICE

TECHNICAL FIELD

The disclosure relates to medical devices and, more particularly, systems and methods for estimating the temperature for outer portions of medical devices.

BACKGROUND

Various devices may be used to treat a variety of medical conditions, deliver therapy, and/or monitor the condition of a patient. In some patients, a device may be implanted within the body of the patient so that the device can then more intimately monitor the condition of the patient and potentially diagnose one or more ailments of the patient in an expedient manner. Example implantable medical devices (IMDs) include implantable neurostimulators (INS), cardiac or cardiovascular implantable electronic devices (CIEDs), implantable cardiac pacemakers, implantable cardioverter-defibrillators (ICDs), spinal cord stimulators, deep brain stimulators, gastrological stimulators, urological stimulators, nerve stimulators, muscle stimulators, infusion devices, cochlear implants, respiratory monitoring implants, orthopedic implants, or any other medical device that may be implanted within a patient in a variety of different ways and for a variety of different health-related reasons.

In cases involving an IMD implanted within the patient, the IMD may include one or more power sources configured to be periodically charged pursuant to a charging process that may be implemented in conjunction with an external charging device. That is, when one of the power sources is depleted, the patient or a caretaker for the patient may use the external charging device to charge the power source. Because the IMD is implanted within the patient, external charging device and the IMD may charge a power source of the IMD pursuant to a wireless charging process, such as a transcutaneous charging process. A transcutaneous charging may be performed via an inductive coupling between a charging coil of the medical device and a corresponding charging coil of the external charging device. In such examples, electrical current flowing through the coils is used to induce an electrical current that the medical device can use to charge the medical device.

SUMMARY

In general, the disclosure is related to devices, systems, and techniques for estimating the external temperature of a device based on one or more sensed temperatures of an internal portion of the device. In particular, a system may determine the temperature of a first internal portion of the device using temperature sensors disposed within the device. The system may then estimate the temperature of a second portion of the device, such as an external portion of a housing of the device, based on an algorithm that incorporates the sensed temperatures of the internal portion of the device. In an example, the external portion of the device represents a part of the device that, when implanted within a patient, contacts tissue of the patient. This external portion may be referred to as an enclosure, case, or shield.

In some examples, the temperature estimation algorithm employed by the implanted medical device or an external device or system may be representative of an estimated temperature difference between an internal portion of the device and an external portion of the device housing and based on a dynamic transfer function that operates in the time-domain (TD). In an example, the system may employ a filter, such as a low-pass filter, that is configured to implement the dynamic transfer function. In some instances, the system may implement the dynamic transfer function as a first-order transfer function. An charging system may then control charging or some other operational aspect related to the implanted medical device based on the estimated temperature of the external portion of the device.

In one example, the disclosure provides a method of determining, via at least one temperature sensor, a temperature of a first portion of a device during a charging process of a power source of the device; estimating, by processing circuitry and based on an algorithm that incorporates the temperature of the first portion of the device, a temperature of a second portion of the device, wherein the algorithm is representative of an estimated temperature difference between the first portion of the device and the second portion of the device based on a dynamic transfer function that operates in a time domain; and controlling, by the processing circuitry and based on the temperature of the second portion of the device, charging of the power source.

In another example, the disclosure provides a system comprising: a memory configured to store temperature data obtained via at least one temperature sensor that is disposed within an internal portion of a medical device; and processing circuitry coupled to the memory and configured to: receive the temperature data, the temperature data being indicative of a temperature of the internal portion of the medical device; and determine an estimated temperature of an external surface of a housing of the medical device based on an algorithm that incorporates the temperature data, wherein the algorithm is representative of an estimated temperature difference between the internal portion of the medical device and the external surface of the medical device based at least in part on a dynamic transfer function that operates in a time-domain.

The disclosure also provides non-transitory computer-readable media comprising instructions that cause a programmable processor to perform any of the techniques described herein. In an example, this disclosure provides a non-transitory computer-readable storage medium having stored thereon instructions that, when executed, cause one or more processors to: determine a temperature sensed by at least one temperature sensor of a first portion of a device; determine, based on an algorithm that incorporates the temperature of the first portion of the device, an estimated temperature of a second portion of the device, wherein the algorithm is representative of an estimated temperature difference between the first portion of the device and the second portion of the device based at least in part on a dynamic transfer function that operates in a time-domain; and control a charging of the power source of the device based on the estimated temperature of the second portion of the device.

In another example, the disclosure also provides means for performing any of the techniques described herein, such as determining a temperature of a first portion of a device during a charging process of a power source of the device; estimating, based on an algorithm that incorporates the temperature of the first portion of the device, a temperature of a second portion of the device, wherein the algorithm is representative of an estimated temperature difference between the first portion of the device and the second portion of the device based on a dynamic transfer function that operates in a time domain; and controlling, based on the temperature of the second portion of the device, charging of the power source.

This summary is intended to provide an overview of the subject matter described in this disclosure. It is not intended to provide an exclusive or exhaustive explanation of the systems, device, and methods described in detail within the accompanying drawings and description herein. Further details of one or more examples of the disclosed technology are set forth in the accompanying drawings and in the description below. Other features, objects, and advantages of the disclosed technology will be apparent from the description, drawings, and claims.

BRIEF DESCRIPTION OF DRAWINGS

Like reference characters denote like elements throughout the description and figures.

DETAILED DESCRIPTION

Figure 1:
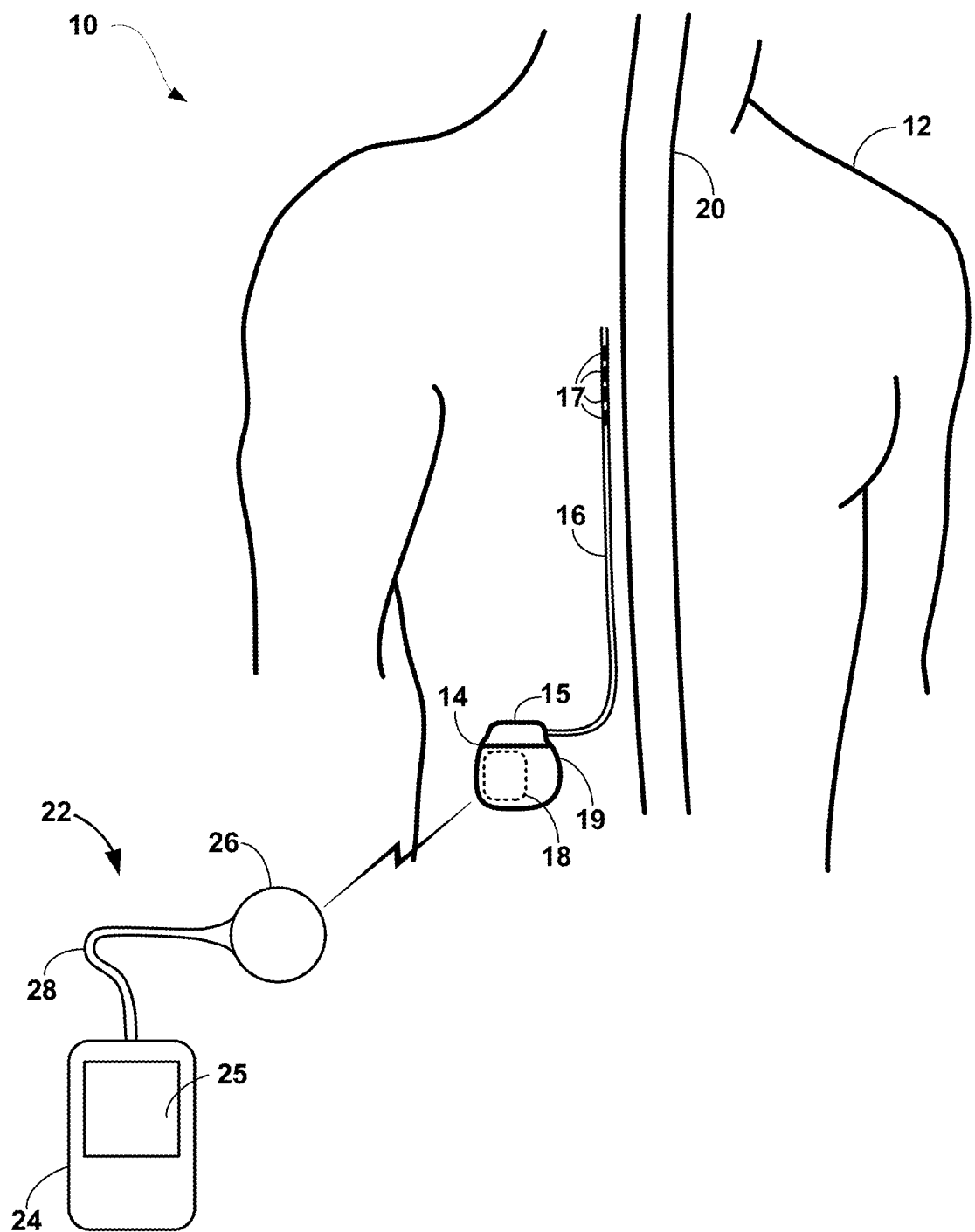
FIG. 1 is a conceptual diagram illustrating an example system that includes an implantable medical device (IMD), an external charging device, and a patient, in accordance with one or more of the various techniques disclosed herein.

This disclosure is generally directed to devices, systems, and techniques for estimating the temperature of an external portion of a device, such as an external housing of an implantable medical device (IMD) or another device. Devices may increase in temperature when receiving power from another device, such as when receiving charging power. It may be beneficial to monitor the external temperature of the device receiving power to avoid undesirable interactions with other materials or environments around the device. For example, IMDs may be implanted within a patient and used to monitor a parameter of the patient and/or deliver a therapy to the patient. To extend the operational life of the IMD, the IMD may include a rechargeable power source (e.g., one or more capacitors or batteries). When the rechargeable power source is being recharged, the power transmitted to the IMD may generate heat that increases the temperature of the IMD. In addition, an external charging device (e.g., another medical device) placed against the skin of the patient may increase in temperature when power is transmitted during the recharging session. This may result in heating of tissue proximate the IMD and/or proximate the external charging device. In order to prevent undesirable temperatures, it may be desirable for the system to monitor sensed temperatures in the IMD and/or external charging device in order to adjust system operation when a temperature reaches a potentially undesirable temperature.

However, it may be difficult to directly measure the temperature of an external surface of the IMD or other device in the transfer of power. An IMD may include a temperature sensor, such as a thermocouple or thermistor, physically attached and thermally coupled to the surface of a target component (e.g., a housing that surrounds the IMD). Alternatively, a thermocouple, thermistor, or other temperature sensor, may be disposed within an IMD to sense the ambient temperature or component or physical element within the IMD. However, thermocouples directly coupled to a desired surface (e.g., an interior surface of the IMD housing) may be difficult and/or expensive to manufacture, and ambient temperature sensors may not accurately measure different temperatures at specific regions of the IMD or portions that transfer heat to the patient. Moreover, in an implanted device, the exterior surface of the IMD housing is not accessible to directly measure temperature.

As described herein, an example system includes a device, such as an IMD, and an external charging device (sometimes referred to as a "medical device charger"). The device generally includes a housing configured to enclose various components of the device and protect components that are disposed within the device from the external environment of the device. In addition, the device includes one or more temperature sensor(s) disposed internally within the device in one or more internal portions of the device. The temperature sensors of the device may be coupled to a circuit board of the device. Circuitry of the board may derive temperature information regarding temperatures sensed within the device. In some examples, the system may further include a remote computing device similarly configured to receive temperature data from the device or from the medical device charger. In any case, the example system may analyze the sensed temperature data representing a temperature of at least one internal portion of the device and estimate the temperature of an external portion of the device based on the sensed temperature data obtained within the device.

During a charging process, the external charging device may generate and transmit power to a power source of the device. The temperature sensor(s) of the device may communicate sensed temperature data to one or more processors of the system, where the sensed temperature data is indicative of the temperature of an internal portion of the device. The system may then estimate the temperature of the second portion of the device based on a temperature estimation algorithm that incorporates the sensed temperature data to determine a temperature estimate for the second portion of the device. The system may adjust the charging process based at least in part on the estimated temperature of the second portion of the device, such as by reducing a charge level of the charging process when the temperature of the second portion of the device as estimated satisfies a temperature level threshold. The temperature level threshold may be predetermined or in some instances, may be a dynamic threshold that adapts to the patient over time. In an example, the temperature level threshold may be preset or adaptively set based on a cumulative thermal dose threshold. The cumulative thermal dose generally refers to a metric used to quantify or estimate the total temperature exposure to tissue that is adjacent to the external surface of the device housing. In some examples, the cumulative thermal dose may be calculated by integrating the tissue temperature over a period of time, where the tissue temperature is inferred based on the temperature estimate for the one or more external portions of the device housing (e.g., at the patient-device interface).

The system may be configured to sense temperatures and estimate temperatures based on sensed temperatures to track thermal states of the device as a dynamic thermal management (DTM) system. In an example, the system may track thermal states of the external structure of the device based on temperature data sensed using one or more temperature sensor(s) disposed within the device. In this way, manufacturing for the device may be simplified to focus on placement of temperature sensor(s) disposed within the device.

In an illustrative example, the temperature sensor(s) may sense the temperature of various heat-generating elements disposed within the device, such as elements of certain electronics disposed within the device. During a charging process of the device, the heat-generating elements may generate heat that may cause the temperature of the device to increase beyond a temperature level threshold preset for the safety and comfort of the patient. The system may process the sensed internal temperature of the device during the charging process, and in response to processing the sensed temperature data obtained via the one or more temperature sensor(s) within the device, the system may estimate the temperature of a second portion of the device based on a dynamic transfer function that operates in the TD. In this manner, the dynamic transfer function may enable the system to determine or estimate the temperature of a portion of the device different from the portion at which the temperature sensor is located or the portion sensed by the temperature sensor.

In response to temperature changes sensed at the first portion of the device and estimated for the second portion of the device, the system may automatically adjust the charging process to maintain the temperature of the second portion of the device within a predefined temperature range. As such, the system may effectively reduce the temperature or rate of temperature change of the second portion of the device by adjusting various control mechanisms of the device or device charger. In another example, the system may effectively decrease the amount of time required for charging the device in instances where the temperature estimated for the second portion of the device is still within a predefined temperature range and is not fluctuating at a rate that the system predicts may result in the temperature of the second portion of the device increasing within a relatively short period of time beyond the temperature level threshold.

In one example, the system is configured to estimate the temperature of the external portion of the device based on one or more temperatures sensed within the device. The one or more temperatures sensed from within the device generally correspond to various internal portions of the device. The internal portions of the device are located inside of the device relative to an external housing for the device. In some examples, the system may estimate the temperature of the external portion of a device housing according to a charging process configured to result in a charging of a power source of the device. In some examples, the power source is disposed within the device and configured for transcutaneous charging.

The system may estimate the temperature of the external portion of the device housing using an algorithm that incorporates the one or more temperature measurements corresponding to the internal portion of the device. In general, the temperature estimation algorithm represents a temperature difference between an internal portion of the device and the external portion of the device based on a predetermined dynamic transfer function that operates in the time-domain. Where the device includes multiple temperature sensors, a unique transfer function may be determined for each temperature sensor of the device, where the transfer function is based on a thermal resistance that may be relatively unique for each temperature sensor of the device.

The charging process for such power sources generally tends to not only affect the temperature of the internal portion of the device, but may also unavoidably affect the temperature of the external portion of the device, where the external portion of the device may be in direct contact with surrounding bodily tissue of a patient. These external portions may be heated through heat transfer from internal components and/or eddy currents generated directly by the charging device. Thus, some temperature increases at the patient-device interface may then cause the surrounding bodily tissue to increase in temperature at a rate proportional to the temperature increase within and around the device. In such examples, the device, or an external charging device coupled to the device and that is configured to charge the device, may monitor the one or more temperatures sensed for the one or more internal portions of the device, as well as the temperature estimated for the one or more external portions of the device housing. Based on such temperature information, the system, including one or both devices, may control the charging process or other device processes to effectively control the temperature of one or more portions of the device, including the internal portion of the device and the external portion of the device.

In performing and utilizing the estimated temperature of one or more external portions of the device housing during the charging process of the device, the system may, in general, prolong the longevity of the device, including components comprising the device, such as the power source of the device, in an advantageous manner. In addition, the system may avoid inadvertent temperature level increases that may occur at the tissue-device interface at levels the system may deem intolerable for the specified functioning of the system components. In an example, the device may control the charging process, or other device processes (e.g., stimulation levels), based on the temperature estimated for the external portion of the device housing. Controlling such processes may effectively maintain the temperature of the device below various temperature level thresholds (e.g., tolerance thresholds). In such instances, the patient may not perceive rising temperatures within the body that may ordinarily be perceived during charging processes where temperature may, in some examples, rise to higher levels.

In an illustrative example, the device may be a medical device that includes a power source configured for transcutaneous charging. Processing circuitry either of the device, or of a system of devices that includes an external charging device and the medical device, may determine a temperature estimate for the external portion of the device during a charging process of the power source. While various temperature estimation aspects are illustrated or described herein with reference to a charging process, it should be understood by a person skilled in the art that the techniques of this disclosure are not so limited. That is, the temperature of the external portion of the device may be estimated irrespective of any charging process in accordance with one or more of the various techniques disclosed herein.

When an external charging device is charging a power source of a medical device (e.g., using inductive coupling), the power transmitted from the external charging device to the medical device may generate heat that tends to increase the temperature of the inside and outside portions of the medical device. The system, including the external charging device and medical device may, in some instances, proactively or otherwise intervene on the charging process. In an example, the system may control the charging process for optimal charging and patient comfort. That is, the system may optimize the charging process using a closed-loop control algorithm that balances charging speeds and health of device components with various parameters, including estimated temperature of an external portion of the housing of the medical device and/or sensed temperatures of various internal portions of the medical device, as feedback for the control algorithm. In any case, the system may estimate the temperature of an external portion of the device in connection with or pursuant to a charging process, such as during or after the charging process when the temperature of the external portion of the device may be most prone to temperature increases.

In another example, a medical device, device charger, or other medical device associated with charging the power source of the medical device, may include one or more temperature sensor(s) for monitoring the temperature of an internal portion of the medical device. Temperature sensor(s) situated internally within the medical device, however, may not be specifically configured to directly sense a temperature of a particular structure of the device because the temperature sensor(s) may not be thermally coupled to the particular structure of the device (e.g., an external surface of the device housing, an internal surface of the device housing, etc.). In accordance with one or more of the various techniques disclosed herein, the system may estimate and monitor the temperature of the outside portion of the device to determine a manner in which to control the charging of the power source and to avoid exposing patient tissue to undesirable device temperatures. The system may estimate the temperature of the outside portion of the device using an algorithm that incorporates temperature data representing a temperature sensed within the device via the one or more temperature sensor(s). In such examples, the algorithm represents a temperature difference between the internal portion of the medical device and external portion of the medical device based on a predetermined dynamic transfer function, such as a transfer function implemented via a low-pass filter (e.g., a first order low-pass filter). In an example, an electronic filter of the medical device, device charger, or other system, may be configured to implement the transfer function as a first-order transfer function that provides a temperature estimate of the external portion of the medical device based on temperatures sensed from within the internal portion of the medical device.

Generally, IMDs may be implanted within a patient and may perform one or more tasks, such as monitoring a parameter of the patient and/or delivering a therapy to the patient. In some examples, the device for which the system estimates the external temperature is an IMD that may, in some instances, be configured for charging by a device charger. That is, to extend the operational life of the IMD, the IMD may include a power source (e.g., one or more capacitors, one or more batteries, etc.) that can be charged over multiple charging cycles. In addition, the IMD may include one or more temperature sensor(s) configured to sense a temperature at a particular portion within the 1 MB. In some examples, the one or more temperature sensor(s) may be configured to provide temperature sensing of the particular portion of the IMD at which the one or more temperature sensor(s) are particularly located. The one or more temperature sensors may include one or more of thermistors, thermocouples, infrared (IR) temperature sensors, or other temperature sensors configured to sense the temperature of one or more portions of a target component within the IMD, such as the temperature of one or more portions of a circuit board disposed within the IMD. In an example, one or more temperature sensors of an 1 MB may be mounted to a printed circuit board (PCB) located within the IMD, or otherwise integrated into the electronic circuitry of the device. Advantageously, a device having temperature sensors integrated with circuitry of the device may be easier to manufacture compared to a device having temperature sensors attached to an external housing of the device. Accordingly, installing the housing of the device to surround the temperature sensor(s) may effectively reduce assembly time, complexity, and cost of producing the device compared to that of other devices that may be configured with temperature sensors installed on an outside of a device housing, rather than on an inside of the device housing.

In accordance with one or more of the various techniques disclosed herein, the temperature sensed in the internal portion of the device may be used to estimate the temperature of another portion of a device, such as the outside portion of the device. The outside portion of the device may be an external surface of a housing of the device that, when disposed within the body of a patient, contacts bodily tissue of the patient. The system may estimate the temperature of the outside portion of the device based on an algorithm that incorporates temperature data relating to a first internal portion of the device. The algorithm may represent a temperature difference between the inner portion of the device and the second outer portion of the device based on a time-domain (TD) transfer function.

FIG. 1 is a conceptual diagram illustrating an example system 10 that includes an example IMD 14 and external charging device 22, in accordance with one or more of the various techniques disclosed herein. In the example of FIG. 1, IMD 14 and external charging device 22 are depicted in conjunction with a patient 12, who is ordinarily, but not necessarily, a human patient. In addition, external charging device 22 may be a computing device with a display viewable by a user. The user, may be a physician, technician, surgeon, electrophysiologist, clinician, caregiver, or patient 12.

A user, such as a clinician or patient 12, may interact with a user interface of an external charging device 22 to program IMD 14, or in some instances, may interact with a user interface of a separate external programmer (not shown) to program IMD 14, such as in instances where external charging device 22 and the external programmer are not implemented as a single combined programmer and charging device. Programming IMD 14 may generally refer to the generation and transfer of commands, programs, or other information to control the operation of IMD 14, e.g., by wireless telemetry or wired connection.

In some examples, external charging device 22 may be included with, or form part of, an external programmer. That is, external charging device 22 may serve the dual role of an external programmer and a charging device. In another example, the external programmer may be implemented as a programmer that is separate from external charging device 22. In any case, a user may program and charge IMD 14 using external charging device 22, or in some examples, using multiple charging devices.

User interface 25 may be configured to receive user input (e.g., via a touch sensitive display or other type of user interface), where the user input may be used to control external charging device 22. In an example, user interface 25 may allow the user to control external charging device 22 based on user input received via user interface 25.

In addition, user interface 25 may be configured to provide output to a user, such as a visual display of information. In an example, user interface 25 may include a display configured to provide information to a user, such as patient 12, related to external charging device 22 and/or a charging process being performed by external charging device 22 in conjunction with IMD 14. In some examples, user interface 25 may include a liquid crystal display (LCD) or a light emitting diode (LED) display. In an example, the display of user interface 25 may include a touch screen display, and a user may interact with external charging device 22 via the display. It should be noted that the user may also interact with external charging device 22 remotely via a network computing device.

IMD 14 may be configured to communicate medical data to external charging device 22. In an example, IMD 14 may communicate with external charging device 22 based on a particular telemetry protocol, Radio-Frequency Identification (RFID) transmission, or other communication techniques. As such, any medical device and/or computing device configured to communicate data to external charging device 22 may be configured to implement the techniques of this disclosure.

External charging device 22 may be configured to charge a power source 18 of IMD 14 via a charging process. Power source 18 may receive a charge from external charging device 22 pursuant to instructions defining the charging process. In turn, IMD 14 may be configured to charge power source 18 pursuant to the charging process implemented via external charging device 22 to periodically recharge power source 18. In some examples, IMD 14 may have a predetermined power capacity (e.g., a power capacity of 12 mAh or less, 80 mAh or more, or other capacities therebetween). In such examples, the charging process of IMD 14 may depend on the power capacity of IMD 14. In some instances, the charging process may further depend on the power capacity of external charging device 22.

In some examples, IMD 14 is implanted within patient 12, such as in a subcutaneous tissue pocket, within one or more layers of muscle, in a thoracic region of patient 12, adjacent and/or along spinal cord 20 of patient 12, etc. Although the techniques described in this disclosure generally apply to a variety of devices (e.g., patient monitors, electrical stimulators, drug delivery devices, etc.), application of such techniques to implantable neurostimulators (INSs) will be described herein for purposes of illustration. More particularly, the disclosure will refer to an INS system for use in spinal cord stimulation therapy, but without limitation as to other types of devices, such as medical devices configured to operate as pacemakers, cardioverters, defibrillators, drug delivery devices configured to deliver therapeutic substances to patient 12, and/or patient monitors.

In some examples, initial values for constants relative to IMD 14 and/or external charging device 22 may be obtained from testing of the devices. In some examples, IMD 14 or external charging device 22 may adjust one or more constants based on system operation or patient specific constraints such as implant depth, IMD 14 orientation, or any other configurations. These constants may be incorporated as part of a temperature estimation algorithm that IMD 14 and/or external charging device 22 may use to estimate the temperature of an external portion of housing 19 based on temperatures sensed relative to one or more internal portions of IMD 14. Such values may be stored to a memory of IMD 14, external charging device 22, or another device of system 10, such as a remote data server (not shown). The devices of system 10 may retrieve such constants from memory to perform one or more of the various temperature estimation techniques disclosed herein.

As illustrated, IMD 14 includes a housing 19 that, in some instances, contacts tissue of patient 12. Housing 19 (sometimes referred to as a "canister" or simply a "can") may be configured to provide a hermetic seal for the various components disposed within housing 19, such as those components described with reference to FIG. 2. As used in this disclosure, housing 19 may comprise a housing and/or other structure(s) that provide one or more external portions of IMD 14. Housing 19 may further include an inside surface that in some instances, is on an opposite side of the outside surface or is at least connected to a portion of housing 19 that forms the external portions of IMD 14.

IMD 14 may have a size (e.g., geometry, weight, dimensions and structuring of housing 19 relative to other components of 1 MB 14, etc.) designed for ease of implant and patient comfort. IMD 14 may be constructed of any polymer, metal, or composite material sufficient to house the components of IMD 14. In some examples, IMD 14 may be constructed with a biocompatible housing, such as titanium, stainless steel, ceramic, or a polymeric material. In an example, housing 19 may be constructed of titanium, stainless steel, ceramic, or another example of a biocompatible material. In an illustrative example, IMD 14 may have a hermetically sealed, biologically inert outer housing or canister which may itself be conductive and thus serve as an electrode. This conductive portion may also serve as a natural source of eddy currents during charging. In addition, IMD 14 is constructed of materials and/or using structures that dissipate heat throughout housing 19 of IMD 14 and/or away from power source 18. In one example in which the external housing composed of ceramics or non-electrically conductive materials (which do not generate eddy currents), the internals of the IMD 14 which do generate eddy currents may rise to higher temperatures than the external surface of the 1 MB.

In some examples, 1 MB 14 and/or external charging device 22 may retrieve power capacity information specified for 1 MB 14 (e.g., the predetermined power capacity of 1 MB 14, etc.). The memories of 1 MB 14 and/or external charging device 22 may be pre-programmed with the power capacity. In an example, 1 MB 14 and/or external charging device 22 may access the power capacity information from a memory system of IMD 14 or from a memory system of external charging device 22. In some examples, IMD 14 and/or external charging device 22 may determine the power capacity of 1 MB 14 based on operational states of either device, power outputs determinable from either device (e.g., an inference determination from an operational state), and/or based on various operational states or determinable power outputs that may be communicated between devices.

Power source 18 may provide operating power to one or more components of IMD 14. In some examples, power source 18 may include a power generation circuit to produce the operating power for operating components of 1 MB 14. Power source 18 of IMD 14 may include one or more capacitors, batteries, or other energy storage devices. Power source 18 may further be rechargeable, such that IMD 14 may replenish, refill, or otherwise increase the amount of energy stored to power source 18. In some examples, power source 18 may be constructed with materials to reduce the amount of heat generated during the charging process of IMD 14. Similarly, housing 19 of IMD 14 may be selected of a material that facilitates the receiving of energy to charge power source 18 of IMD 14.

In some examples, power source 18 may be disposed within IMD 14. While an implantable power source 18 is generally described herein, the techniques disclosed herein are not so limited, and a person skilled in the art will understand that the techniques disclosed herein may also be applicable to a power source 18 that is not an implanted power source. In an example, power source 18 may be externally located relative to housing 19. In such examples, power source 18 may be separately protected from fluids of patient 12. In another example, power source 18 may be external to the skin of patient 12 and/or in physical contact with the skin. When IMD 14 and/or power source 18 is external to patient 12, external charging device 22 may still control the charging of power source 18, such as based on temperature(s) sensed within charging head 26 or within IMD 14. In any case, power source 18 may be configured to be electrically coupled to components of IMD 14 so as to provide operational power for IMD 14.

In some examples, IMD 14 may deliver stimulation energy to one or more locations within patient 12 via a lead 16, or in some instances, a plurality of leads. As shown, lead 16 is configured to carry one or more electrodes 17. In some examples, lead 16 may be configured to deliver stimulation energy generated by IMD 14 to stimulate one or more nerves of patient 12. A program that controls delivery of the stimulation energy may identify particular configurations of electrodes 17 for delivery of stimulation energy. In an example, stimulation energy may be delivered in the form of electrical stimulation, such as stimulation pulses or continuous waveforms. In some examples, IMD 14 is configured to deliver electrical stimulation to patient 12 via a combination of electrodes 17.

In the example of FIG. 1, electrodes 17 of lead 16 may be placed adjacent to spinal cord 20 for spinal cord stimulation therapy. In some examples, electrodes 17 may include electrode pads on a paddle lead, ring electrodes, conformable electrodes, cuff electrodes, or segmented electrodes at different circumferential positions around lead 16. As described, lead 16 and IMD 14 may, in some instances, be configured to additionally or alternatively provide drug therapy. In some examples, lead 16 may be configured to provide deep brain stimulation, gastric stimulation to treat obesity or gastroparesis, tibial nerve stimulation, or other deep tissue or more superficial types of electrical stimulation. In some examples, lead 16 may tunnel through tissue of patient 12. In an example, lead 16 may tunnel from along spinal cord 20 to an internal location of patient 12 to couple to other components of IMD 14. In some examples, lead 16 may include a header block 15 that couples lead 16 to IMD 14. In various examples, header block 15 may be considered as part of housing 19.

External charging device 22 may be a hand-held device, a portable device, or a stationary charging system used to charge the power source 18. In one example, the external charging device 22 may take the form of a charging mat which is placed over a chair or as part of a mattress pad. In other examples, the external charging device 22 may contain all the electronics in a single handheld device and may communicate with additional equipment wirelessly for supplemental user interface (such as a commercial-off-the-shelf handset). External charging device 22 may include a user interface 25. User interface 25 may include touch screen features, buttons, or a keypad provided by user interface 25 that allow the user to provide user input. External charging device 22 may be configured to receive, via user interface 25, user input from a user. In some examples, external charging device 22 may be implemented as an external programmer, such as a physician programmer, clinician programmer, or patient programmer.

In some examples, external charging device 22 may be implemented as an external programmer, such as an external programmer configured to transmit programming commands to IMD 14 in addition to charging power source 18. In another example, external charging device 22 may communicate with IMD 14, such as by transmitting information to and/or receiving information from IMD 14. The information communicated may include information related to the charging of power source 18. For example, IMD 14 may transmit information including temperature data (e.g., sensed and/or estimates), an amount of power received during the charging process, the charge level of power source 18, charge current rates, power source voltage, etc.

External charging device 22 may include components necessary to charge power source 18 through tissue of patient 12. For example, external charging device 22 may include housing 24, charging cable 28, and a charging head 26. Housing 24 may contain at least some of the operational components of external charging device 22. Charging cable 28 may electrically couple charging head 26 to the power source within housing 24, such that charging cable 28 may transmit power and/or information to charging head 26. In an example, the charging cable may be unnecessary and the charging head 26 may be included in the housing 24 of the external charging device 22. Charging head 26 may include a coil for inductive coupling of components used to transmit power from charging head 26 to power source 18. Although a user may control the charging process with a user interface, such as user interface 25 of external charging device 22, charging may alternatively be controlled by another device (e.g., an external programmer).

External charging device 22 and IMD 14 may utilize any wireless power transfer techniques that are capable of charging power source 18 of IMD 14 when IMD 14 is implanted within patient 12. In one example, system 10 may utilize inductive coupling between a coil of external charging device 22 (e.g., a coil within charging head 26) and a coil of IMD 14 coupled to power source 18. In inductive coupling, external charging device 22 is placed near implanted IMD 14 such that a primary coil of external charging device 22 is aligned with a secondary coil of IMD 14, such as by being placed over the secondary coil of IMD 14, for example. External charging device 22 may then generate an electrical current in the primary coil based on a power level selected for charging power source 18. As further described below, the power level may be selected to control the temperature of IMD 14, along with the charge rate of power source 18. When the primary and secondary coils are at least partially aligned, the electrical current in the primary coil may induce an electrical current in the secondary coil within IMD 14 and in turn, increases the voltage, or charge level, of power source 18. Although inductive coupling is generally described herein, any type of wireless energy transfer may be used to charge power source 18. In such cases, the system may allow adjusting the charging speed of the system or maximum temperature during charging.

During the charging process, some of the energy may be converted into heat at power source 18, at other components of IMD 14, such as housing 19, and/or in charging head 26, for example. When increased energy levels are used to charge power source 18 at a higher rate, the temperature of IMD 14 and/or external charging device 22 may increase at a proportional rate. Although the temperature of the external portion(s) of housing 19 may not achieve a temperature sufficient to burn, necrose, or otherwise affect tissue adjacent to, for example, housing 19 of IMD 14, elevated temperatures may still be undesirable and could, in some cases, cause discomfort for patient 12.

As described herein, system 10 may utilize one or more temperature sensors to measure or otherwise sense the temperature of a portion of a device, such as an external portion of housing 19 of IMD 14. In one example, temperature sensor(s) of system 10 may sense the temperature of a portion of a medical device (e.g., charging head 26 or an internal portion of IMD 14) via a direct measurement. The temperature sensors(s) of system 10 are not limited to any particular type of temperature sensor, and may include one or a combination of temperature sensors, such as a thermistor, a thermocouple, a resistance thermometer, or a proportional-to-the-absolute-temperature (PTAT) temperature sensor. The one or more temperature sensors may be arranged to sense a temperature of some portion of IMD 14, such as an internal portion of IMD 14. In another example, a phase change material (or other thermally conductive material or pad) may be used to facilitate temperature sensing of one or more components of IMD 14. The phase change material may be disposed on the surface of a component from which temperature is to be sensed (e.g., a circuit board of IMD 14). In some examples, the phase change material may be encapsulated by a membrane, embedded in a woven fabric, or otherwise disposed in at least partial contact with a surface of the component. In an example, thermally conductive epoxy or grease may be used between interfaces within the IMD to reduce the thermal resistance between two portions or to affix the temperature sensor(s) to a surface.

In some examples, one or more devices of system 10 may estimate and/or monitor temperatures of any device or component that may come into contact with or otherwise affect tissue of patient 12. These estimated and/or monitored temperatures may be used as feedback in a temperature control system. For example, external charging device 22 may control the power level, power cycle times, and/or charging time used to charge power source 18 to reduce or minimize any undesirable temperatures of IMD 14. In addition, monitoring the temperature of IMD 14, including monitoring the estimated temperature of housing 19, may allow IMD 14 and/or external charging device 22 to effectively minimize patient discomfort and ensure an effective charging process.

In an illustrative example, the one or more temperature sensors include temperature sensors, such as a silicon bandgap temperature sensor, that may be incorporated directly into one or more integrated circuits mounted to a circuit board enclosed within IMD 14, and arranged to sense a temperature of the electrical circuits and/or the ambient temperature adjacent to the electrical circuits within housing 19.

Processing circuitry included in system 10 (e.g., one or more processors housed by either external charging device 22, IMD 14, or both) may be configured to control charging of power source 18 based on the estimated temperature of a particular portion of housing 19, such as an external portion of housing 19. In an example, the temperature of the external portion of housing 19 may be estimated based on a dynamic transfer function and based on the temperatures provided by the one or more temperature sensors disposed within IMD 14 and/or in conjunction with one or more temperature sensors disposed with external charging device 22.

Temperature measurements from temperature sensor(s) within IMD 14 (e.g., temperature sensor(s) not thermally coupled to any external portion of housing 19) may be used to estimate the temperature for one or more external portion(s) of housing 19. The estimated temperature of housing 19 may then be used for controlling the charging of power source 18. For example, external charging device 22 may control the electrical current flowing through a primary coil within charging head 26 based on the estimated temperature of housing 19. External charging device 22 may control a current, for example, by controlling a current amplitude, duty cycle, or other characteristic of the charging current. Utilizing the estimated temperature of housing 19 based on one or more of the various techniques disclosed herein, for example using the algorithms disclosed herein, may allow for a more aggressive recharging regime. For example, utilization of the estimated temperature for controlling the charging process may allow using higher power levels for more extended periods of times during the charging process, thus reducing the overall charging time.

The temperature sensors (e.g., non-thermally coupled or non-contact sensors) discussed herein are generally described as non-thermally coupled to the portion or surface of a structure of IMD 14 from which the temperature will be estimated. In other words, the temperature sensor may not use physical contact or other direct measurements to sense the temperature of an external portion of the device (e.g., an external hotspot portion of IMD 14 or another medical device). Although the temperature sensor(s) within IMD 14 may be physically connected or mounted through one or more structures to the housing of IMD 14, the temperature of the external portion of the housing is not sensed or measured directly through this physical connection via the temperature sensors within IMD 14 as a result of inherent thermal resistances within the device.

In some examples, temperature sensor(s) 39 (FIG. 2) may be integrated as part of a hybrid board of IMD 14. In an example, the hybrid board may be in thermal communication with a surface of housing 19. As such, the temperature sensor, although perhaps configured to measure the temperature of a particular component of the hybrid board, such as a power transformer, may still be able to sense the surface temperature of an internal portion of housing 19, but only to a very limited degree of accuracy. In an example, the temperature sensor of the hybrid board may sense the internal surface temperature of housing 19 through an interfering medium other than the hybrid board, such as through air or another gas separating the temperature sensor or the hybrid from the internal portion of housing 19. As a person of skill in the art would understand, such temperature sensor(s) disposed within the device (e.g., on or as part of a circuit board of the device) may not be able to accurately sense the temperature for any surface of housing 19, including internal and external surfaces of housing 19.

In some examples, IMD 14 may include a single temperature sensor. In another example, IMD 14 may include a plurality of temperature sensors. In an example, charging head 26 (e.g., external of patient 12) and/or IMD 14 (e.g., implanted within patient 12) may each include one or more temperature sensors. Multiple temperature sensors may be provided within the same device for various reasons. In an example, each of the multiple temperature sensors may be configured to sense the temperature of the same portion of the device for redundant, backup, composite, or cross-correlated temperature measurements. In addition, certain devices of IMD 14 may be configured to provide ancillary temperature measurements, such as a temperature measurement received from an accelerometer of IMD 14. In this example, the accelerometer may include or otherwise serve as a type of temperature sensor configured to sense the temperature of an internal portion of IMD 14.

In some examples, two portions of IMD 14 being sensed for temperature may be located adjacent to each other (e.g., different locations of a generally planar surface). In an example, two temperature sensors may be mounted to the same side of a circuit board (e.g., a hybrid circuit board, a PCB, etc.). The temperature sensors may be oriented toward various surfaces of IMD 14. In another example, the two surfaces may be generally opposed to one another, such as two surfaces separated by a circuit board that is carrying a plurality of temperature sensors. In this example, each temperature sensor may be mounted on opposing sides of the circuit board. In such examples, a first temperature sensor of IMD 14 may be configured to sense temperatures relative to a first side of the circuit board of IMD 14, and a second temperature sensor may be configured to sense temperatures relative to a second side of the circuit board of IMD 14. In any case, a plurality of temperature sensors of IMD 14 may be configured to sense temperatures simultaneously. In this way, system 10 may process multiple temperatures that are sensed from within IMD 14 at approximately the same time.

In some examples, one or more temperature sensors of IMD 14 may be selectively enabled and disabled, for example, by processing circuitry of IMD 14. Such selective temperature sensing may reduce power consumption from unnecessary temperature sensors. In addition, selective temperature sensing may reduce power consumption and/or processing speed needed to process signals from one or more disabled temperature sensors.

In some examples, external charging device 22 may access IMD information, such as configuration details of IMD 14 (e.g., power capacity information, IMD size, operating state, etc.). In such examples, external charging device 22 and/or IMD 14 may adjust various parameters of the charging process and/or coefficients involved in the temperature estimation process for a particular portion of IMD 14 (e.g., exterior surface of housing 19). In some examples, the temperature estimation process includes estimating a temperature of housing 19 based on an algorithm that incorporates temperature measurements obtained from one or more temperature sensor(s) that are disposed within IMD 14. In such examples, the algorithm represents a temperature difference between at least two separate portions of IMD 14 based on a dynamic transfer function. The two portions may include a first portion located within a predetermined range of one or more temperature sensors disposed within IMD 14 and a second portion that, in some examples, corresponds to an external surface of housing 19. In some examples, the coefficients involved in the temperature estimation process for IMD 14 may include coefficients corresponding to heat capacity of housing 19 and/or coefficients corresponding to internal components of IMD 14. The coefficients may include filter coefficients for a filter, such as a low-pass filter, configured to filter a temperature signal corresponding to the first portion of IMD 14 to estimate the temperature of the second portion of IMD 14 based on a dynamic transfer function (e.g., a first order transfer function). In some examples, IMD 14 may take into account information from other sensors such as acceleration or position sensors to determine a spatial orientation of IMD 14 to the charger.

System 10 may control the charging of power source 18 using one or more techniques. Using the estimated temperature for a portion of housing 19 (e.g., exterior surface of housing 19 at one or more locations of housing 19), processing circuitry may compare the estimated temperature to a temperature level threshold. The sensed temperature may be from a temperature sensor located within IMD 14 and/or external charging device 22. The temperature level threshold may be a value stored by a memory located within IMD 14 and/or within external charging device 22. The temperature level threshold may be selected based on tissue models, patient history, user selected charging speed or temperature, or any other information that may be used to determine when a charging process should be modified. The processing circuitry may then determine when the estimated temperature of housing 19 and/or exterior surface(s) of housing 19 exceeds the temperature level threshold. When the estimated temperature exceeds the temperature level threshold, the processing circuitry may control charging of power source 18 by adjusting a power level used to charge power source 18. In other words, the processing circuitry may reduce the power level when the temperature level threshold is exceeded, turn the power off for a predetermined period of time before the power is again provided (e.g., cycle the power on and off) or even terminate the charging process.

Reducing the power level may reduce the energy used to charge power source 18 and/or the rate at which power source 18 is charged. In some examples, control of the charging process may be based on the temperature estimate for housing 19 that is estimated based on the temperature estimation algorithm that incorporates one or more temperatures sensed via the one or more temperature sensor(s) that are disposed within IMD 14.

In some examples, when sensing a temperature of a component of IMD 14, the processing circuitry of IMD 14 may transmit temperature data (e.g., sensed temperature values, estimated temperature values, etc.) to external charging device 22. As such, processing circuitry of external charging device 22 may, in some examples, estimate the temperature of housing 19 using one or more of the various techniques disclosed herein, and/or any equivalents thereof, to determine a manner in which to control the charging process. Alternatively, the processing circuitry of IMD 14 may determine a manner in which to control the charging process for IMD 14 and may transmit a command to external charging device 22 to instruct external charging device 22 control the charging process in a particular manner as defined by the command.

In some examples, external charging device 22 may charge power source 18 using one or more power levels or cycle times. In some examples, external charging device 22 may select a "high" power level when starting a charging process. External charging device 22 may then select a "low" power level, relative to the "high" power level, in response to one or more estimated temperature(s) related to housing 19 increasing above a temperature level threshold. In this manner, the "high" power level may charge power source 18 at a high rate to reduce charging time while increasing the temperature of IMD 14. External charging device 22 may select the "low" power level to charge power source 18 at a slower rate to effectively reduce the temperature of housing 19. The "low" power level may be sufficiently minimal so that any increase in temperature of housing 19 may have minimal or no effect on surrounding tissue.

A "high" power level and a "low" power level may be subjective and relative to the charging power that external charging device 22 is capable of generating and transmitting to IMD 14. In some cases, the "high" power level may be the maximum power that external charging device 22 can generate. By estimating the surface temperature of one or more external portions of housing 19 and controlling the charging process in response to the estimated temperature, external charging device 22 may charge power source 18 with the "high" power level for a longer period of time so long as the estimated temperature does not exceed a temperature level threshold.

In an example, the "high" power level may be 2.5 Watts and the "low" power level may be less than 0.5 Watts (W). Other power levels and ranges may be selected for use. An example charge current level may be 100 milliamps (mA) for the "high" power level and 60 mA for the "low" power level. An example primary coil voltage and current for a "high" power level may be 450 V and 800 mA. An example primary coil voltage and current for a "low" power level may be 250 V and 500 mA. In other examples, the primary coil voltage and current may be some combination of values that achieve 3.0 W or less for high power or 0.5 W or less for low power. These values are merely examples, and other examples may include higher, lower, or otherwise different power level values. In addition, a plurality of different power levels may be defined to control charging pursuant to the charging process.

In some cases, external charging device 22 may cycle the driving of the primary coil. For instance, external charging device 22 may drive the coil during a first time period, and may discontinue driving the coil for a second time period following the first time period to control an overall transmission of power and in effect, heat generation/dissipation within and around housing 19.

In some examples, IMD 14 may directly adjust the power level for charging IMD 14. In an example, as IMD 14 receives a charging current during the charging process of IMD 14, IMD 14 may employ a circuit that may toggle from full-wave to half-wave rectification so as to adjust the charge rate, and in turn, effectively control the temperature of one or more external portions of housing 19. In another example, IMD 14 may employ current and/or voltage limiters that may adjust the charging rate of power source 18.

As described herein, one or more temperature sensor(s) may be used to sense a temperature of an internal portion of IMD 14, including power source 18 and/or electronic circuitry enclosed within IMD 14. Based on the estimated temperature of an external portion of housing 19, processing circuitry of system 10 may control an aspect of the charging process. The processing circuitry of system 10 may be housed by housing 19, charging head 26, or housing 24. The processing circuitry configured to perform some, or all of the functions described herein may be housed together with one or more temperature sensor(s), for example within IMD 14, or separately from the temperature sensor(s), for example as part of external charging device 22, an external programmer, or a remote server (e.g., a cloud-based network server).

In an example, the system may estimate the temperature of the second portion of the device based on an algorithm that incorporates the temperature of the first portion of the device to estimate the temperature of the second portion of the device. In some examples, the algorithm may represent a temperature difference between the first portion of the device and the second portion of the device based on, for example, a discrete-time implementation of a low-pass filter (LPF) that incorporates the temperature of the first portion of the device to estimate the temperature of the second portion of the device. In some examples, the TD transfer function may include a first-order transfer function. In this way, the system may estimate the temperature of an external portion of the device using temperature data obtained via one or more temperature sensor(s) located within a housing of the device. The system may thus be configured to estimate the temperature of an external portion of the device without being thermally-coupled (with low thermal resistance) to the second portion of the device.

The devices, system 10, and techniques disclosed herein allow for the estimation of the temperature of a housing or other exterior surface of an 1 MB. In some examples, the medical device, or an external charging device used for charging the medical device, may be able to estimate a temperature of a portion of the IMD based on a first-order transfer function that incorporates one or more temperature(s) sensed from within at least one internal portion of the medical device. In some examples, various processes may be employed to estimate these temperatures from the measured temperature of the temperature sensor based on a dynamic transfer function and/or a static transfer function. By controlling the charging of the 1 MB based on the estimated temperature of the housing of the 1 MB, the 1 MB and/or the external charging device may provide faster charging while also maintaining safe operating temperatures for patient 12.

In some instances, system 10 may track the estimated temperature of the second portion of the device over time to determine whether the temperature of housing 19 remains within a temperature range conducive to continual use of the device within a heat-sensitive environment, such as within the body of a patient. As such, the system may effectively manipulate the temperature of the second portion of the device based on the thermal state of the device, where the thermal state of the device may fluctuate in response to a charging process configured to charge a power source of the device. Charging may have a calculable influence on the thermal state of the second portion of the device in such a way that varying the charging state of the device may then have a specific effect on the manipulation of the temperature of the second portion of the device.

Figure 2:
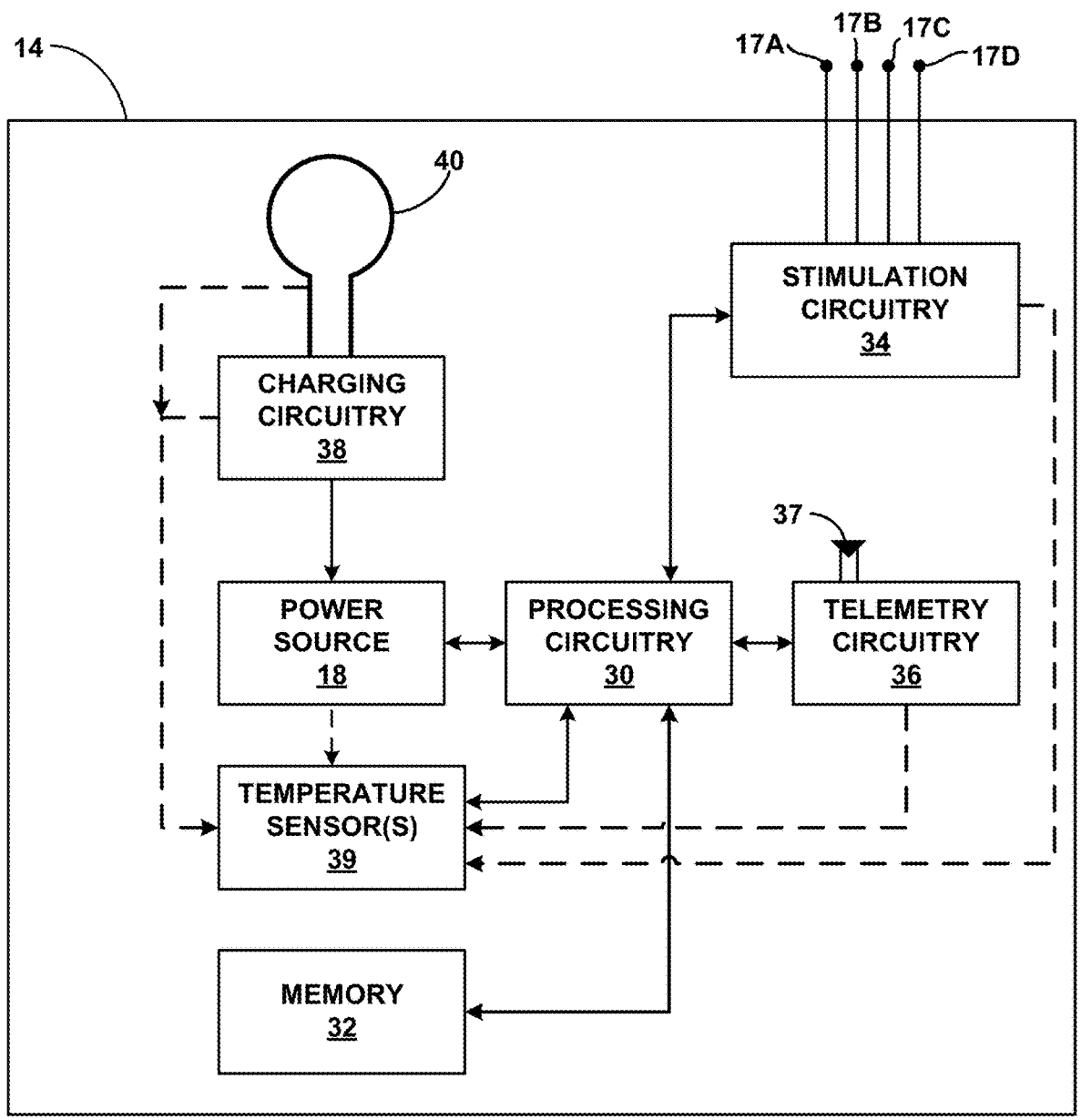
FIG. 2 is a block diagram of an example IMD, in accordance with one or more of the various techniques disclosed herein.

FIG. 2 is a block diagram illustrating example components of IMD 14, in accordance with one or more of the various techniques disclosed herein. In the example illustrated in FIG. 2, IMD 14 includes one or more temperature sensor(s) 39, secondary coil 40, processing circuitry 30, stimulation circuitry 34, charging circuitry 38, telemetry circuitry 36, and a power source 18. While IMD 14 is illustrated as having a certain number of components, the techniques of this disclosure are not so limited, and IMD 14 may include a greater or a fewer number of components than shown in FIG. 2. In addition, IMD 14 may comprise any suitable arrangement of hardware, alone or in combination with software and/or firmware, to perform one or more of the various techniques of this disclosure attributed to circuitry or other components of IMD 14, and any equivalents thereof.

As shown, IMD 14 includes memory 32. Memory 32 may include a short-term memory device, a long-term memory device, or both a short-term memory device and a long-term memory device. In some examples, memory 32 may include one or more of random access memory (RAM), read only memory (ROM), programmable read only memory (PROM), erasable PROM (EPROM), electronically erasable PROM (EEPROM), non-volatile RAM (NVRAM), dynamic RAM (DRAM), static RAM (SRAM), magnetic discs, optical discs, flash memory, a hard disk, or any other digital media. Memory 32 may be used to store data indicative of instructions for execution by processing circuitry 30. In such examples, memory 32 may include a computer-readable storage medium that stores executable instructions configured to cause, when executed, processing circuitry 30 and/or other components of IMD 14 to perform one or more of the various techniques of this disclosure ascribed to such circuitry or other components of IMD 14, and/or any equivalents thereof.

Temperature sensor(s) 39 may include one or more temperature sensors configured to sense the temperature of various internal portions of IMD 14. As described herein, temperature sensor(s) 39 may not be thermally coupled to, and may not be directly attached to, the portion of housing 19 for which a temperature is to be estimated. In other words, temperature measurements are not performed through direct contact or physical contact between temperature sensor(s) 39 and the target portion to be estimated (e.g., an external portion of housing 19, a portion of an internal surface of housing 19). Although temperature sensor(s) 39 may be physically attached to the target portion or target surface through one or more structures, thermal conduction occurring between the target portion and temperature sensor(s) 39 via the one or more structures is not directly used to measure the temperature of the target portion. As such, processing circuitry 30 may estimate the temperature of the target portion of housing 19 based on temperature measurements obtained via temperature sensor(s) 39, in cases where measuring the temperature of the target portion directly is not practical via temperature sensor(s) 39.

Temperature sensor(s) 39 may be arranged to measure the temperature of a component, surface, or structure of IMD 14, such as power source 18, charging circuitry 38, and/or other components of IMD 14 disposed within housing 19. As such, temperature sensor(s) 39 may be used to obtain temperature measurements for one or more internal portions of IMD 14, the internal portions of IMD 14 including components of IMD 14, such as a circuit board or other electronics of IMD 14 that are disposed within housing 19. The internal portions of IMD 14 may further include the internal space of IMD 14 that surrounds, or is otherwise proximate, temperature sensor(s) 39, such as space within a predefined temperature sensing range of temperature sensor(s) 39.

In some examples, temperature sensor(s) 39 may be used to obtain temperature measurements of header block 15 as an example internal portion of IMD 14. In any case, temperature sensor(s) 39 may be configured to obtain temperature measurements that processing circuitry 30 may utilize to estimate temperatures of an external portion of housing 19 (e.g., an external portion of header block 15). Although a single temperature sensor 39 may be adequate, multiple temperature sensors 39 may provide more specific temperature readings of separate components or of different portions of IMD 14.

In some examples, processing circuitry 30 may continuously measure temperature using temperature sensor(s) 39. In another example, processing circuitry 30 may conserve energy by only measuring temperatures during a particular period of time, such as during a charging process for IMD 14. Further, temperatures may be sampled at a rate necessary to effectively control the charging process, where the sampling rate may be reduced to conserve power as appropriate.

In some examples, memory 32 may store programs or other instructions that specify parameter values for the control of IMD 14 and/or external charging device 22. In an example, memory 32 may store temperature data from temperature sensor(s) 39, thresholds (e.g., temperature tolerance thresholds), instructions for charging power source 18, or any other instructions required to perform tasks attributed herein to IMD 14 or external charging device 22. Furthermore, memory 32 may be configured to store instructions for communicating with and/or controlling one or more of temperature sensor(s) 39. In various examples, memory 32 stores information related to the estimation of the temperature of housing 19, such as one or more external portion(s) of housing 19.

In some examples, memory 32 may store one or more formulas, as further described herein, that may be used to estimate the temperature of housing 19. Memory 32 may store values for one or more determined constants used by these formulas. In some examples, memory 32 may store instructions that, when executed by processing circuitry such as processing circuitry 30, cause the processing circuitry to perform an algorithm, including using one or more formulas, to estimate a temperature for housing 19, such as one or more external portion(s) of housing 19. In an example, processing circuitry 30 may perform the algorithm to estimate the temperature of an external surface of IMD 14, such as one or more of the external portions of housing 19, during a charging process of IMD 14 and/or for some time after the charging process.

In some examples, memory 32 may store filter coefficients that the algorithm may incorporate in estimating a temperature of a particular portion of housing 19 based on the temperature sensed at another portion of IMD 14 by one or more internally displaced temperature sensor(s) 39. In an example, memory 32 may store cutoff frequency values, constants, formulas, gain values, transfer functions, transfer function coefficients. In addition, memory 32 may store convolution properties that define a convolution function configured to convolve a plurality of transfer functions, etc.

In some examples, processing circuitry 30 of IMD 14 may include one or more processors that are configured to implement functionality and/or process instructions for IMD 14 to execute. In an example, processing circuitry 30 may be configured to access memory, such as memory 32, to retrieve information comprising instructions, formulas, determined values, and/or one or more constants. In addition, processing circuitry 30 may be configured to process instructions retrieved from memory 32. As such, processing circuitry 30 may use the retrieved information to execute a temperature estimation algorithm that provides an estimate of a current temperature, and/or a time-series of estimated temperatures, for one or more external portions of housing 19 based on a dynamic transfer function.

In some examples, processing circuitry 30 may include one or more microprocessors, digital signal processors (DSPs), application specific integrated circuits (ASICs), field-programmable gate arrays (FPGAs), complex programmable logic devices (CPLDs), or any other equivalent integrated or discrete logic circuitry, as well as any combinations of such components. Accordingly, IMD 14 may include any suitable structure, whether in hardware, software, firmware, or any combination thereof, to perform the functions ascribed herein to IMD 14, and processing circuitry 30, telemetry circuitry 36, charging circuitry 38, stimulation circuitry 34, and/or equivalents thereof. In an example, processing circuitry 30 of IMD 14, and/or the processing circuitry of external charging device 22, may implement any of the techniques described herein to receive and/or analyze temperature data sensed by temperature sensor(s) 39, and/or by temperature sensor(s) of external charging device 22, to then estimate a temperature of an external portion of housing 19. In addition, processing circuitry of IMD 14, or external charging device 22, may control the charging process of IMD 14 based on a determination of a temperature estimate of housing 19 exceeding a temperature level threshold.

Although processing circuitry 30, stimulation circuitry 34, charging circuitry 38, telemetry circuitry 36, and temperature sensor(s) 39 may be described or shown as separate, the techniques of this disclosure are not so limited, and a person skilled in the art would understand that some combination of processing circuitry 30, stimulation circuitry 34, charging circuitry 38, telemetry circuitry 36 and temperature sensor(s) 39 may, in some examples, be functionally integrated in combined devices. In some examples, stimulation circuitry 34, charging circuitry 38, telemetry circuitry 36, and temperature sensor(s) 39 may correspond to hardware units, such as ASICs, DSPs, FPGAs, CPLDs, or other hardware units.

In some examples, stimulation circuitry 34 generates and delivers electrical stimulation under the control of processing circuitry 30. Example stimulation parameters include voltage amplitude, electrical current amplitude, pulse rate, pulse width, duty cycle, and/or combinations of electrodes 17A, 17B, 17C, and 17D (collectively "electrodes 17"). Alternatively, or additionally, IMD 14 may be configured to provide different therapy to patient 12. For example, IMD 14 may be configured to deliver drug therapy via a catheter. These and other therapies may be provided by IMD 14.

IMD 14 also includes components to receive power from external charging device 22 to charge power source 18. As shown in FIG. 2, IMD 14 includes secondary coil 40 and charging circuitry 38 coupled to power source 18. Charging circuitry 38 may be configured to charge power source 18 with a selected power level determined by either processing circuitry 30 or external charging device 22.

Charging circuitry 38 may include one or more circuits that process, filter, convert and/or transform the electrical signal induced in secondary coil 40 to an electrical signal capable of charging power source 18. In an example, charging circuitry 38 may convert electrical current that was induced in secondary coil 40 into charging current to then charge power source 18. In some examples, charging circuitry 38 may include a rectifier circuit. In some examples, charging circuitry 38 may be configured to toggle between rectifier circuits to control the charge rate for power source 18 and effectively control the temperature of the external portion of housing 19. In some examples, processing circuitry 30 may be configured to provide commands to charging circuitry 38 to control one or more aspects of the charging process.

Secondary coil 40 may include a coil of wire or other device capable of inductive coupling with a primary coil of external charging device 22. Although secondary coil 40 is illustrated as a simple loop in FIG. 2, secondary coil 40 may include multiple turns of conductive wire. Secondary coil 40 may include a winding of wire configured such that an electrical current can be induced within secondary coil 40. The electrical current induced in secondary coil 40 may be used to charge power source 18. The induction may be caused by electrical current generated in the primary coil of external charging device 22, where the level of the electrical current generated in the primary coil may be based on an adjustable power level of the charging process.

Although inductive coupling is generally described as the method for charging power source 18, the techniques disclosed herein are not so limited, and a person skilled in the art will understand that other wireless energy transfer techniques may be used. Any of these techniques may generate heat in IMD 14. As such, processing circuitry of IMD 14 or of external charging device 22 may control the charging process of IMD 14 based on the estimated temperature of an external portion of housing 19 of IMD 14 based on, for example, a dynamic transfer function that estimates the temperature of the outer surface of IMD 14 based on one or more temperatures determined from temperature sensor(s) 39 disposed within IMD 14.

In some examples, processing circuitry 30 be configured to control the exchange of information with external charging device 22 and/or an external programmer using telemetry circuitry 36. Telemetry circuitry 36 may be configured for wireless communication using radio frequency protocols or inductive communication protocols. Telemetry circuitry 36 may include one or more antennas 37 configured to communicate with external charging device 22 or another device (e.g., a network device, a remote server, etc.). Processing circuitry 30 may transmit operational information and receive therapy programs or therapy parameter adjustments via telemetry circuitry 36. Also, in some examples, IMD 14 may communicate with other implanted devices, such as electrical stimulators, control devices, or sensors, via telemetry circuitry 36. In addition, telemetry circuitry 36 may be configured to control the exchange of information related to sensed and/or estimated temperature data.

In some examples, processing circuitry 30 may transmit additional information to external charging device 22 related to the operation of power source 18. In an example, processing circuitry 30 may use telemetry circuitry 36 to transmit indications that power source 18 is completely charged, power source 18 is fully discharged, or any other charge status of power source 18. In some examples, processing circuitry 30 may use telemetry circuitry 36 to transmit instructions to external charging device 22, including instructions regarding further control of the charging process, such as instructions that when executed cause external charging device 22 to alter the power level or to terminate the charging process, based on the estimated temperature of housing 19. In another example, processing circuitry 30 may transmit information to external charging device 22 that indicates any problems or errors with power source 18, charging circuitry 38, or any other device.

In some examples, processing circuitry 30 may receive, via telemetry circuitry 36, instructions for algorithms, including formulas and/or values for constants to be used in the formulas, that processing circuitry 30 may utilize to estimate the temperature of one or more external portions of housing 19. As described herein, processing circuitry 30 may utilize a temperature estimation algorithm that incorporates temperatures sensed via temperature sensor(s) 39 and that represents, for example, a temperature difference between a particular internal portion of IMD 14 that coincides with a first temperature sensor 39 and a particular external portion of housing 19 of IMD 14.

Processing circuitry of system 10 (e.g., processing circuitry 30 of IMD 14, processing circuitry 50 of external charging device 22, etc.) may infer the temperature of tissue surrounding housing 19. In an example, processing circuitry 30 may use the temperature estimated for housing 19 to infer the temperature of tissue surrounding housing 19. In some examples, external charging device 22 and/or IMD 14 may use the inferred temperature of the tissue of patient 12, or the estimated temperature of an external portion of housing 19, to adjust the charging process of IMD 14 and effectively alter the temperature of housing 19.

Figure 3:
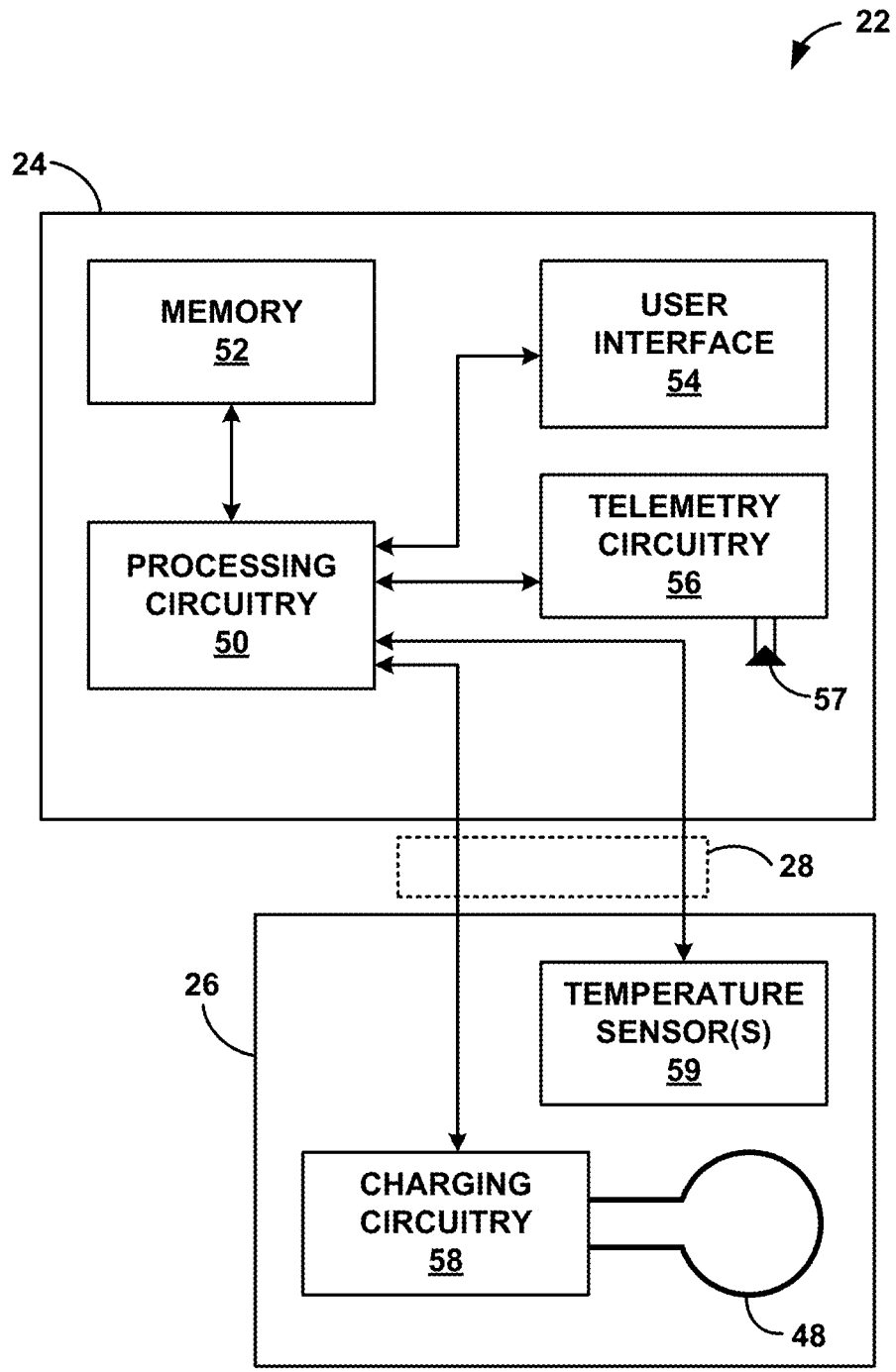
FIG. 3 is a block diagram of an example external charging device, in accordance with one or more of the various techniques disclosed herein.

Although power source 18, charging circuitry 38, and secondary coil 40 are shown as being disposed within housing 19, the techniques of this disclosure are not so limited, and a person skilled in the art would understand that in some examples, various components of IMD 14 may be disposed outside of housing 19. In an example, secondary coil 40 may be disposed outside of housing 19, such as to facilitate better coupling between secondary coil 40 and primary coil 48 of external charging device 22 (FIG. 3). A person skilled in the art would understand that different configurations can allow IMD 14 to be implanted in various anatomical spaces.

In an example, IMD 14 may comprise an additional housing (not shown) that is separate from housing 19 that contains some components of IMD 14. In such examples, processing circuitry 30 may be configured to estimate the temperature of a plurality of external portions of IMD 14 based on internally sensed temperatures, where the estimated temperatures include a temperature estimated for an external portion of housing 19 and a temperature estimated for an external portion of the additional housing of IMD 14. Such estimates may be determined based at least in part on temperature data sensed via temperature sensor(s) 39.

FIG. 3 is a block diagram of an example external charging device 22. While external charging device 22 may generally be described as a hand-held device, external charging device 22 may, in some instances, be a relatively larger device or more stationary device. In some examples, external charging device 22 may be included as part of an external programmer, include functionality of an external programmer, or may be configured to communicate with a physically separate external programmer (not shown).

In some examples, external charging device 22 has two separate components. In a first component, housing 24 encloses components such as processing circuitry 50, memory 52, user interface 54, and telemetry circuitry 56. In a second component, charging head 26 encloses charging circuitry 58, temperature sensor(s) 59, and a primary coil 48. In example involving two separate components, housing 24 may be coupled to charging head 26 via charging cable 28. In another example, charging circuitry 58, temperature sensor(s) 59, and/or primary coil 48 may be disposed within housing 24. In such examples, housing 24 incorporates charging head 26.

In addition, external charging device 22 includes a memory 52, such as one or more of a short-term memory or a long-term memory. In such examples, memory 52 may include one or more of RAM, ROM, PROM, EPROM, EEPROM, NVRAM, DRAM, SRAM, magnetic discs, optical discs, flash memory, a hard disk, or any other digital media. Memory 52 may store data indicative of instructions for execution by processing circuitry, such as processing circuitry 50. In an example, memory 52 may include a computer-readable storage medium configured to store executable instructions that, when executed, cause processing circuitry 50 and/or other components of external charging device 22 to perform one or more of the various functions ascribed to such circuitry and components throughout this disclosure, and/or any equivalents thereof.

In an example, memory 52 may include instructions that cause processing circuitry 50 to control the power level used to charge IMD 14. The instructions may cause processing circuitry 50 to estimate a temperature for housing 19 based on temperatures sensed via temperature sensor(s) 39 and/or based on temperatures sensed via temperature sensor(s) 39 and temperature sensor(s) 59. In response to the estimated temperature of housing 19 satisfying a predetermined temperature level threshold, the instructions may cause processing circuitry 50 to execute corrective action tasks in an attempt to lower the temperature of housing 19 to below a temperature level threshold. In any event, memory 32 and/or memory 52 may include instructions that cause processing circuitry 30 and processing circuitry 50 to determine a temperature estimate for an external portion of housing 19 or charging head 26, in accordance with one or more of the various techniques disclosed herein.

In some examples, memory 52 may be configured to store instructions for communicating with temperature sensor(s) 39 and/or temperature sensor(s) 59. In an example, memory 52 may include instructions configured to cause processing circuitry 50 to control, via telemetry circuitry 56, charging cable 28, or wiring inside IMD 14, one or more temperature sensor(s) 39 or 59 by following a particular communication protocol established between devices.

In some examples, memory 52 may store information related to the temperature estimation algorithm, where the estimation algorithm, when executed, causes processing circuitry 50 or processing circuitry 30 to estimate the outer temperature for one or more external portions of housing 19. The algorithm may do so by incorporating one or more temperatures sensed via one or more of temperature sensor(s) 39 or 59 to estimate the temperature of one or more external portions of housing 19 or charging head 26 in some examples. The algorithm may further result in an estimate of the external temperature by incorporating information relating to the thermodynamics of IMD 14 or other devices related to charging such as charging head 26. The thermodynamics information may be learned over time based on data obtained via IMD 14 and/or external charging device 22, such as by using a machine learning (ML) or artificial intelligence (AI) algorithm to train IMD 14 or external charging device 22 to better understand the thermodynamics of system 10. In another example, the thermodynamics information may be determined prior to the implantation of 1 MB 14 within patient 12. In a non-limiting example, the information relating to the thermodynamics of IMD 14 may include a thermal resistance value representative of the relative heat conductance, or lack thereof, for certain materials used to assemble 1 MB 14, such as the material used to manufacture housing 19.

In some examples, the estimation algorithm stored to memory 52 may, when executed, incorporate a temperature value sensed via a temperature sensor 39 to then estimate a temperature for housing 19 by utilizing a dynamic transfer function that corresponds specifically to the temperature sensor 39. That is, each of temperature sensor(s) 39 may include a transfer function (e.g., a single transfer function, a combination of transfer functions) that is unique relative to each other temperature sensor 39 because the transfer function for the estimation algorithm. The transfer function for each temperature sensor 39 may include a single transfer function or a combination of transfer functions (e.g., a convolution of transfer functions).

In an example, memory 52 may store one or more formulas, as further described below, that may be used to estimate the temperature of an external portion of housing 19. In addition, memory 52 may store values for one or more determined constants used by these formulas. In addition, memory 52 may include data records, including records indicative of power levels related to the charging of power source 18, temperatures sensed via temperature sensor(s) of IMD 14, temperatures sensed via temperature sensor(s) of external charging device 22, a first temperature estimated for one or more first external portions of housing 19, a second temperature estimated for one or more second external portions of housing 19, or any other data related to system 10 or the charging process for a device of system 10, such as the charging process for IMD 14 implanted within patient 12 or in some cases, for a non-implantable medical device.

In some examples, processing circuitry 50 may receive a request to transmit a particular set of data to IMD 14 or to another computing device, such as a remote data server. In an example, the other computing device may be configured to communicate temperature data between devices over a computing network, store temperature data in a storage device, and/or manipulate temperature data to determine various temperature estimates relative to the medical device. In response to receiving the request, processing circuitry 50 may transmit the data set to another device pursuant to the received request. In some examples, the data set includes one or more temperature values sensed via temperature sensor(s) 39 and/or in some instances, one or more temperature values estimated based on one or more temperature values sensed via temperature sensor(s) 39. Responsive to the request, processing circuitry 50 may transmit the particular data set, via telemetry circuitry 56, to IMD 14. In another example, processing circuitry 50 may, when requested, transmit, via telemetry circuitry 56, data to or back to IMD 14 or to another computing device for review and/or for further processing. In some examples, processing circuitry 50 may be configured to access memory, such as memory 32 of IMD 14 and/or memory 52 of external charging device 22, to retrieve information comprising instructions, formulas, and determined values for one or more constants, and to use this information to execute an algorithm to estimate the temperature of housing 19. In another example, memory 52 and/or memory 32 may store variables, constants (e.g., heat capacity, thermal resistances, device size, thermal pad information, etc.), coefficients, parameters, transfer function(s), convolved transfer functions, operational states (e.g., thermal states, dynamic thermal states), etc. In an example, the transfer functions for individual temperature sensor(s) to their respective external temperatures could be individually calibrated at time of manufacturing for each IMD 14 or external charging device 22.

In another example, memory 52 may store instructions that, when executed by processing circuitry, such as processing circuitry 50, causes the processing circuitry to perform an algorithm, including using the formulas, to estimate the temperature of housing 19 during a charging process of IMD 14 and/or for some time after the charging process has concluded. In some examples, memory 52 may store instructions that, when executed by processing circuitry, such as processing circuitry 50, cause the processing circuitry to determine a value to be assigned to one or more of the constants used in the temperature estimation algorithm.

Processing circuitry 50 of external charging device 22 may include one or more processors that are configured to implement functionality and/or process instructions for external charging device 22 to execute. In an example, processing circuitry 50 may be configured to process instructions stored in memory 52. In some examples, processing circuitry 50 may include one or more microprocessors, DSPs, ASICs, FPGAs, CPLDs, or any other equivalent integrated or discrete logic circuitry, as well as any combinations of such components. Accordingly, external charging device 22 comprises any suitable arrangement of hardware, alone or in combination with software and/or firmware, to perform the functions ascribed herein to external charging device 22, and processing circuitry 50, user interface 54, telemetry circuitry 56, and charging circuitry 58 of external charging device 22, and/or any equivalents thereof.

As shown, external charging device 22 may include one or more temperature sensor(s) 59. Temperature sensor(s) 59 may obtain temperature data for analysis and/or transmitting to IMD 14 or another device. Temperature sensor(s) 59 may, in some cases, be similar to temperature sensor(s) 39, for example, described with reference to FIG. 1. As an illustrative example, temperature sensor(s) 59 and temperature sensor(s) 39 may both include thermistors, thermal diodes, and/or any other type of temperature sensing device configured to obtain sensed temperature data, and in some instances, communicate the temperature data to processing circuitry 50 for analysis. In some examples, temperature sensor(s) 59 and temperature sensor(s) 39 are used to safely control the skin-facing temperature of external charging device 22. In another example, external charging device 22 may use temperature sensor(s) 39 to diagnose device faults in charging circuitry 58, telemetry circuitry 56, or other devices of external charging device 22, such as failure modes associated with primary coil 48, a power source of external charging device 22 (not shown), and so forth.

In some examples, temperature sensor(s) 59 may be disposed within charging head 26 and/or within housing 24. In some examples, temperature sensor 59 may be disposed within charging head 26 and oriented to sense the temperature of the housing of charging head 26. In another example, temperature sensor(s) 59 may be disposed within charging head 26 and oriented to sense the temperature of charging circuitry 58 and/or primary coil 48. In some examples, external charging device 22 may include multiple temperature sensor(s) 59 each oriented to any of these portions of device to manage the temperature of the device during the charging process of IMD 14. In some examples, external charging device 22 does not include any temperature sensor(s) 59.

User interface 54 may include a button or keypad and a display; it may also include light emitting diodes (LEDs) or a speaker. Processing circuitry 50 may present and receive information relating to the charging of power source 18 via user interface 54. In an example, processing circuitry 50 may be configured to receive user input via user interface 54. In another example, processing circuitry 50 may indicate via user interface 54 when charging is occurring, a quality of the alignment between secondary coil 40 and primary coil 48, the one or more power levels for the charging process, the charge level of power source 18, sensed temperatures and/or estimated temperatures of IMD 14, etc. In some examples, processing circuitry 50 may receive some of the information displayed on user interface 54 from IMD 14 via telemetry circuitry 56.

In some examples, external charging device 22 includes components to transmit power to power source 18. As shown in FIG. 3, external charging device 22 includes primary coil 48 and charging circuitry 58. Charging circuitry 58 may be configured to generate an electrical current in primary coil 48. Although primary coil 48 is illustrated as a simple loop in FIG. 3, primary coil 48 may include multiple turns of wire. Charging circuitry 58 may generate the electrical current according to a power level selected by processing circuitry 50 or processing circuitry 30. The power level may be based on temperature data received from IMD 14 (e.g., sensed temperature(s) and/or estimated temperature(s)). In addition, the power level may be based on temperatures sensed or estimated via temperature sensor(s) 59 of external charging device 22. In some examples, processing circuitry 50 may select a "high" power level, a "low" power level, or power levels therebetween to control the charge rate of power source 18. In this way, processing circuitry of system 10 may effectively alter the temperature of one or more external portion(s) of housing 19 by systematically controlling an amount of heat generated during the charging process.

Primary coil 48 may include a coil of wire or other devices capable of inductive coupling with secondary coil 40 of IMD 14. Primary coil 48 may include a winding of wire configured such that an electrical current generated within primary coil 48 can produce a magnetic field configured to induce an electrical current within secondary coil 40. The induced electrical current may then be used to charge power source 18. In this manner, the electrical current may be induced in secondary coil 40 associated with power source 18. In some examples, user interface 54 of external charging device 22 may provide one or more audible tones or visual indications of the alignment of primary coil 48 and secondary coil 40.

In some examples, processing circuitry 50 may control charging circuitry 58 based on a power level selected by processing circuitry 30 of IMD 14. The temperature of the external portion of housing 19 may be estimated from a temperature sensed by temperature sensor(s) 39 of IMD 14. Although processing circuitry 50 may control the power level used for charging power source 18, charging circuitry 58 may include processing circuitry including one or more processors configured to partially or fully control the power level based on the sensed and/or estimated temperatures of IMD 14.

In some examples, charging circuitry 58 may include one or more circuits configured to facilitate the transfer of power to charge power source 18 via primary coil 48. In some examples, charging circuitry 58 may be configured to generate an electrical current to flow through primary coil 48 pursuant to a predetermined power level. In some examples, charging circuitry 58 may specify wattage, electrical current amplitude, voltage amplitude, pulse rate, pulse width, a cycling rate, and/or a duty cycle, or any other parameter that may be used to modulate the power transmitted from primary coil 48. In this manner, each power level may include a specific parameter set that specifies the signal for each power level. Changing from one power level to another power level (e.g., a "high" power level to a lower power level) may include adjusting one or more parameters. For instance, at a "high" power level, primary coil 48 may be substantially continuously driven, whereas at a lower power level, primary coil 48 may be intermittently driven such that periodically the coil is not driven for a predetermined time. The parameters of each power level may be selected based on hardware characteristics of external charging device 22 and/or IMD 14. In an example, primary coil 48 and secondary coil 40 may be made of non-hygroscopic materials (e.g., polypropylene, polystyrene, etc.). In such examples, external charging device 22 and/or IMD 14 may be able to control the charging process differently than if one or both coils were made of hygroscopic materials.

Telemetry circuitry 56 supports wireless communication between IMD 14 and external charging device 22 under the control of processing circuitry 50. In some examples, telemetry circuitry 56 includes any suitable hardware, firmware, software or any combination thereof for communicating with another device, such as IMD 14. Under the control of processing circuitry 20, telemetry circuitry 56 may receive downlink telemetry from, as well as send uplink telemetry to, IMD 14, or another device. In some examples, processing circuitry 50 may transmit data, via telemetry circuitry 56, to IMD 14, and in some instances, may transmit data as a relay of data back to IMD 14 that reflects data sent previously to external charging device 22. In an example, processing circuitry 50 may transmit temperature data to IMD 14 that includes temperatures sensed via temperature sensor(s) 39 and/or temperatures estimated for an external portion of IMD 14 based on the temperatures sensed via temperature sensor(s) 39. Telemetry circuitry 56 may also be configured to communicate with devices other than IMD 14 via any of a variety of forms of wired and/or wireless communication and/or network protocols.

In some examples, telemetry circuitry 56 may include an antenna 57. Telemetry circuitry 56 may be configured to communicate with IMD 14 or another computing device via wireless communication techniques or direct communication through a wired connection. Telemetry circuitry 56 may be substantially similar to telemetry circuitry 36 of IMD 14. Although external charging device 22 and/or IMD 14 may include antennas for telemetry, the techniques of this disclosure are not so limited, and external charging device 22 and/or IMD 14 may also be configured to utilize inductive coupling from secondary coil 40 and primary coil 48 to transfer data (e.g., sensed temperature data, estimated temperature data, estimated temperature data paired with corresponding sensed temperature data, etc.). In some examples, external charging device 22 and IMD 14 may communicate with one another or with any other device via near-field communication (NFC) technologies, far-field communication technologies, electromagnetic coupling, radio frequency (RF) communication, Bluetooth®, Wi-Fi™, or other proprietary or non-proprietary wireless communication schemes, and/or may inductively communicate.

As described herein, telemetry circuitry 56 may be configured to receive a signal or data representative of a sensed temperature from IMD 14 and/or an estimated temperature of housing 19. The estimated temperature may be estimated using an algorithm, including use of formula(s) as described herein, that incorporates temperatures measured of one or more internal portion(s) of IMD 14, such as circuitry mounted to a circuit board disposed within IMD 14, and that represents a temperature difference between the external portion of housing 19 and the one or more internal portion(s) of IMD 14 based on a dynamic transfer function, such as a transfer function implemented via an LPF (e.g., a first order LPF).

In some examples, multiple temperature readings by IMD 14 may be averaged or otherwise used to produce a single temperature value that is transmitted to external charging device 22. In an example, IMD 14 may transmit a temperature measurement from a temperature sensor that is reading a higher temperature during the charging process relative to other temperature sensors 39. In addition, the sensed and/or estimated temperature may be sampled and/or transmitted by IMD 14 (and received by external charging device 22) at different rates. Processing circuitry 50 may then use the received temperature information to control charging of power source 18 (e.g., control the charging level used to charge power source 18).

Although processing circuitry 50, telemetry circuitry 56, charging circuitry 58, and temperature sensor(s) 59 are described as separate, in some examples, processing circuitry 50, telemetry circuitry 56, charging circuitry 58, and/or temperature sensor 59 are functionally integrated. In addition, in some examples, processing circuitry 50, telemetry circuitry 56, charging circuitry 58, and/or temperature sensor 59 correspond to individual hardware units, such as ASICs, DSPs, FPGAs, or other hardware units.

Figure 4:
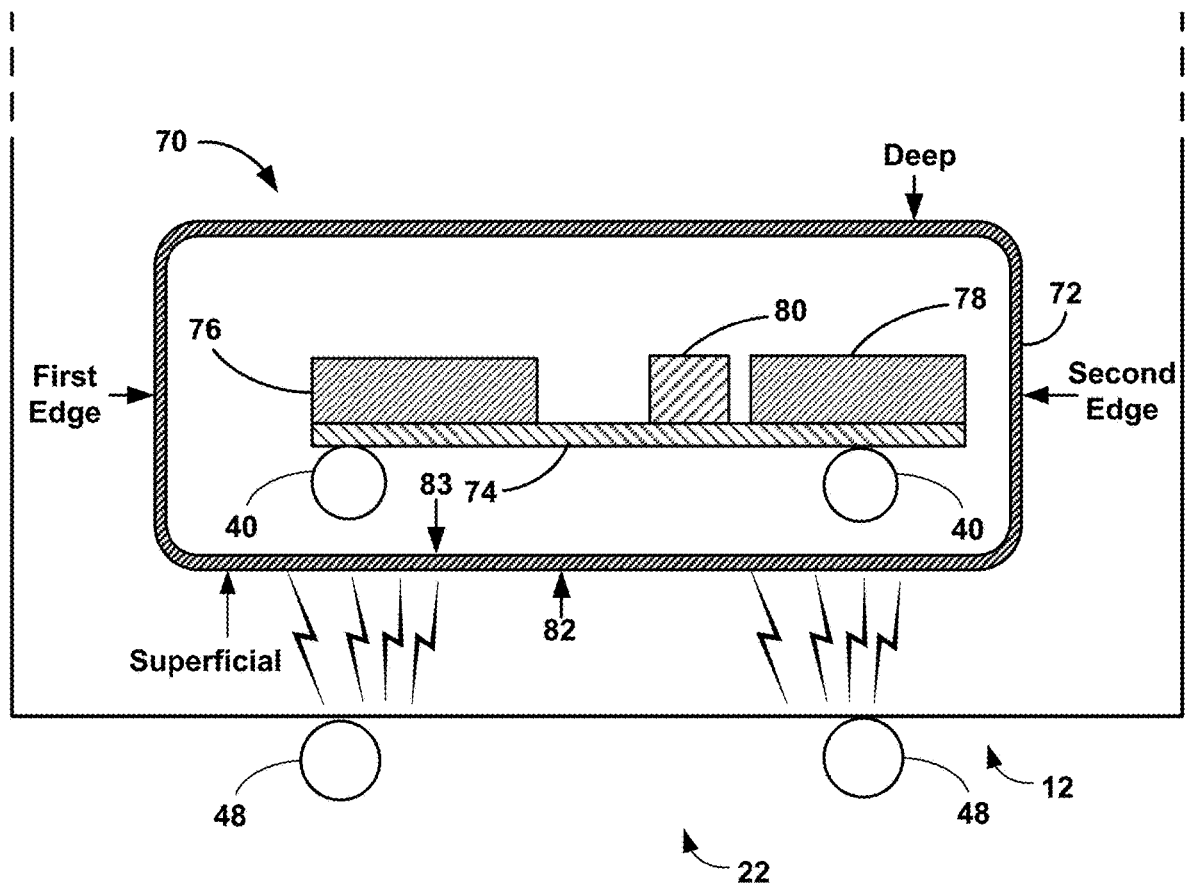
FIG. 4 is a cross-sectional diagram of an example IMD, in accordance with one or more of the various techniques disclosed herein.

FIG. 4 is a cross-sectional diagram illustrating an example IMD 70, in accordance with one or more of the various techniques disclosed herein. 1 MB 70 includes a housing 72 and a temperature sensor 80 disposed within housing 72. IMD 70 may be an example of 1 MB 14 and temperature sensor 80 may be an example of temperature sensor(s) 39. The 1 MB described with reference to FIG. 4 is generally shown with a rectangular cross-section. However, temperature sensor 80 may be disposed within an 1 MB, or any other device, of any suitable device proportions.

As shown in FIG. 4, housing 72 includes an exterior surface 82 and an interior surface 83. Housing 72 encloses circuit board 74, electronic circuits 76 and 78, and temperature sensor 80, within the interior of 1 MB 70. Exterior surface 82 may, in some examples, include various external portions of housing 72 as shown, including a deep portion (e.g., facing inwardly or deep relative to the skin of patient 12 and external charging device 22 during the charging process), edge portions, and/or a superficial portion (e.g., facing outwardly or superficial relative to the skin of patient 12 and external charging device 22 during the charging process). Interior surface 83 may similarly include various internal portions, such as a first internal portion proximate temperature sensor 80. In an example, the first internal portion may be within a particular temperature sensing range predetermined for temperature sensor 80. The range may be predetermined for temperature sensor 80 based on the actual temperature sensing range of temperature sensor 80 that allows temperature sensor 80 to provide accurate data readings based on an accuracy criterion.

Circuit board 74 may, in some examples, be a PCB, a hybrid integrated circuit, a hybrid attached to a PCB, a multi-function-chip integrated circuit (MFIC), or any other circuit board. Circuit board 74 may be mounted or secured within housing 72. Electronic circuits 76, 78 may be mounted to circuit board 74, or comprise hybrid circuit boards mounted to circuit board 74. Electronic circuits 76 and 78 may include various components such as processing circuitry and/or memory. In an example, electronic circuits 76 and 78 may include components described further with reference to FIG. 2, such as processing circuitry 30, memory 32, charging circuitry 38, stimulation circuitry 34, telemetry circuitry 36, temperature sensor(s) 39, etc. That is, although temperature sensor 80 is illustrated in FIG. 4 as being physically separate from electronic circuits 76, 78, in some examples temperature sensor 80 may be directly physically coupled to, integrated with, or otherwise incorporated with one or both of electronic circuits 76 and/or 78. In addition, IMD 70 may further include a secondary coil (e.g., each side of secondary coil 40) and power source (e.g., power source 18) disposed therewithin the interior of housing 72.

In some examples, temperature sensor 80 may be incorporated with circuit board 74, such as by being mounted onto a surface of circuit board 74, integrated together with circuitry of circuit board 74, or disposed upon or within circuit board 74. In addition, temperature sensor 80 is not limited to any particular type of temperature sensor. Temperature sensor 80 may, for example, be a thermistor, a thermocouple, a resistance thermometer, or a silicon bandgap temperature sensor. In an example, temperature sensor 80 may be a thermopile composed of two or more thermocouples. In another example, temperature sensor 80 may include a thermal diode. In some examples, temperature sensor 80 may be a dual-range temperature sensor. In an example, temperature sensor 80 may be configured to provide a first sensing range and a second sensing range. In such examples, one sensing range may be more accurate than the other sensing range for temperature sensor 80. In any case, temperature sensor 80 would not be in direct thermal conduction with housing 72. As such, temperature sensor 80 is not configured to sense a temperature of exterior surface 82 of IMD 70, but instead is used to provide a sensed temperature measurement of an internal portion of IMD 70 proximate temperature sensor 80, such that external charging device 22 or IMD 70 may estimate the temperature of one or more external portions of housing 72.

In an illustrative example, processing circuitry of external charging device 22 or IMD 70 (e.g., IMD 14) may estimate the temperature of one or more external portions of housing 72 based on temperature readings obtained via temperature sensor 80. The one or more external portions may be those portions that are prone to allowing more heat to flow into the body of patient 12 over a particular period of time during the charging process relative to other external portions of IMD 70 that may instead be configured so as to sufficiently absorb, redirect, or otherwise dissipate heat such that the temperature of housing 72 at those particular portions will not exceed a temperature level threshold.

The one or more external portions of housing 72 that are prone to allowing more heat to flow into the body of patient 12 may, in some instances, be referred to as "hot spot(s)" indicating that the one or more external portions of housing 72 are prone to allowing more heat to flow into the body of patient 12 relative to other portions of housing 72 that would not flow the same amount of heat into the body of patient 12 under the same conditions. Hot-spots are prone to changing positions of the external charger 22 relative to the exterior surface 82 of IMD 70. Hot-spots may change based on various factors. In an example, a hot spot may migrate across exterior surface 82 in response to IMD 70 flipping to a new device orientation within patient 12 (e.g., a back portion of IMD 70 now becomes the front, outwardly facing portion, misalignment of external charger 22 and IMD 70, relative coplanarity of IMD 70 relative to the skin, etc.).

In another example, temperature sensor 80 may be configured to sense a temperature associated with circuit board 74 (e.g., temperatures of electronic circuits 76, 78). The sensed temperature(s) provided by temperature sensor 80 may be processed in accordance with one or more of the various techniques disclosed herein, or any equivalents thereof. In an example, processing circuitry of external charging device 22 or IMD 70 (e.g., IMD 14) may utilize the sensed temperature(s) obtained via temperature sensor 80 to estimate the temperature for one or more external portions of exterior surface 82 of housing 72. IMD 70 and/or external charging device 22 may utilize the estimated temperature(s) and/or a time-series of estimated external temperatures to control the charging process of a power source disposed within IMD 70 (e.g., power source 18).

Figure 5:
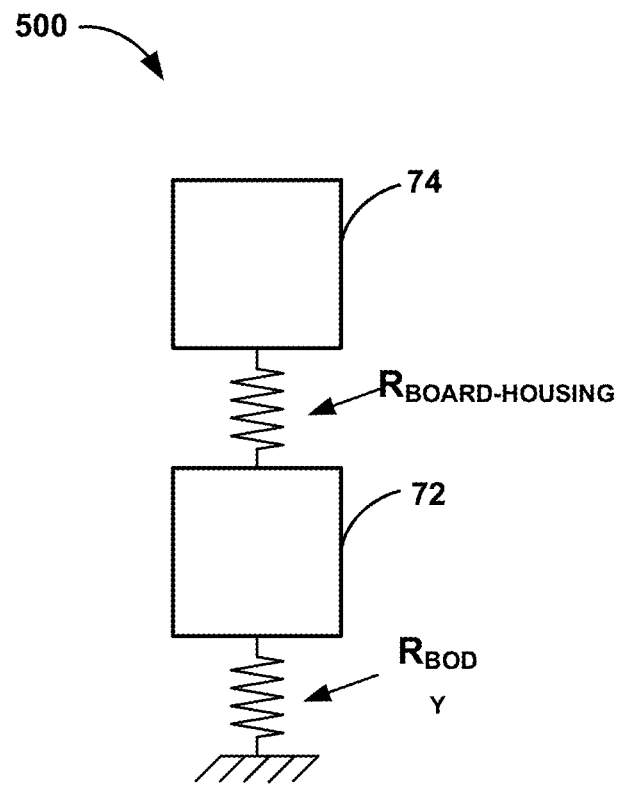
FIG. 5 is a conceptual diagram of a thermal circuit model, in accordance with one or more techniques of this disclosure.

FIG. 5 is a block diagram of a thermal circuit model 500, in accordance with one or more of the various techniques disclosed herein. As shown, thermal circuit model 500 is a simplified thermal circuit model for an example two-body system that includes components of IMD 70 (e.g., IMD 14). Regardless of the exact position of temperature sensor(s) 39 within IMD 70 (e.g., IMD 14), IMD 70 and/or external charging device 22 may use the sensed temperatures from temperature sensor(s) 39 to estimate the temperature of housing 72 (e.g., housing 19). External charging device 22 or IMD 14 may estimate the temperature of housing 19 based on a plurality of transfer functions, such as a dynamic transfer function, a static transfer function, or a combination of the dynamic transfer function and the static transfer function. These transfer functions are able to translate temperatures internal to IMD 14 to temperatures at the tissue contacting surface of housing 19 of IMD 14. In an example, these transfer functions are implementable in real-time embedded firmware in external charging device 22.

The two-body system includes circuit board 74 and housing 72 of FIG. 4 with a first thermal resistance value from a first internal portion of IMD 70 that corresponds to circuit board 74 and housing 72 denoted in FIG. 5 as $R_{BOARD\text{-}HOUSING}$. In addition, a second thermal resistance value from housing 72 to the body of patient 12 is denoted as $R_{BODY}$.

Figure 6:
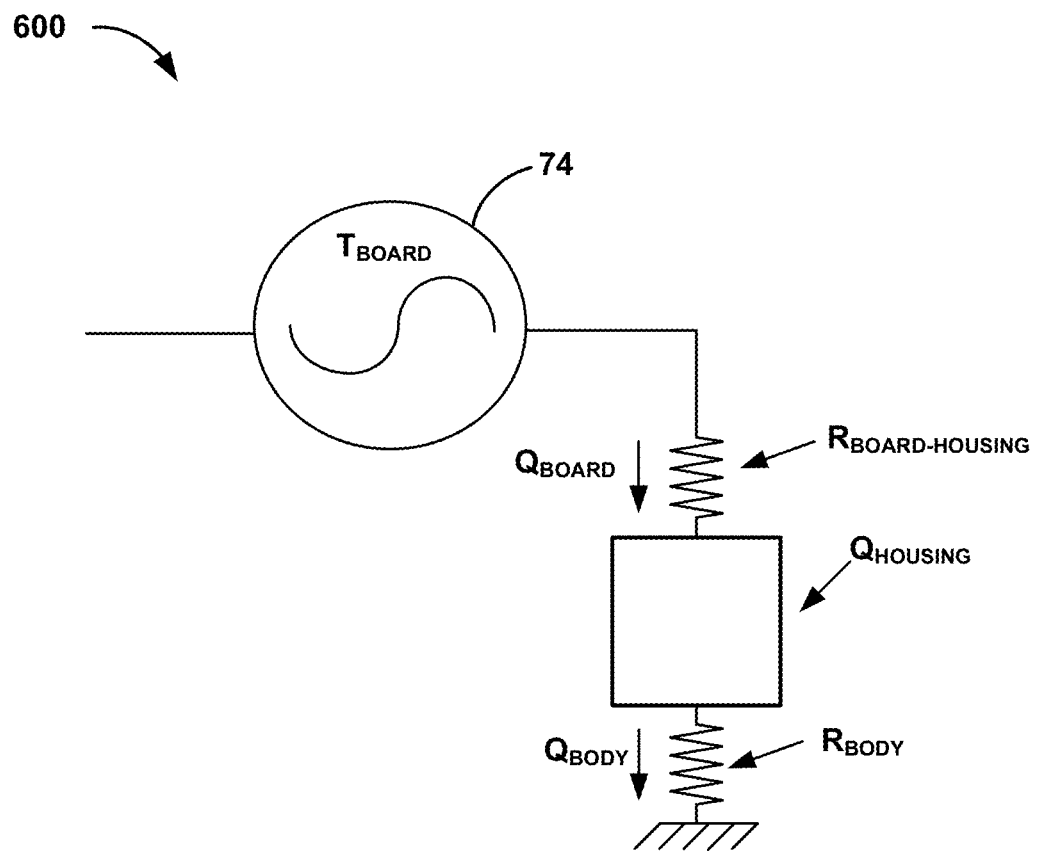
FIG. 6 is a conceptual diagram of an example thermal circuit model, in accordance with one or more of the various techniques disclosed herein.

FIG. 6 is a block diagram of a thermal circuit model 600, in accordance with one or more of the various techniques disclosed herein. Thermal circuit model 600 provides an illustration of thermal circuit model 500 with a heat flow, where heat is generally denoted with the letter 'Q' as a person of ordinary skill in the art would understand. Thermal circuit model 600 represents a simplified system model. This simplified system model is created with an assumption that the circuit board of IMD 14 effectively operates as a source of thermal energy for housing 19. Additionally, thermal circuit model 600 may operate under a so-called "hot spot" assumption.

Thermal circuit model 600 represents a heat source that is internal to IMD 14 and that contributes to increasing the temperature of an external portion of housing 19. The heat source in this example is circuit board 74 and/or electronics located on circuit board 74. Circuit board 74 with temperature sensor 80 as in FIG. 4 operates as a heat source having a thermal frequency.

In some examples, processing circuitry, e.g., processing circuitry 30 of IMD 14, or processing circuitry 50 of external charging device 22, may employ a dynamic transfer function for system 10. For each time-step of the dynamic transfer function, the dynamic transfer function may be expressed:

$$T_{HOUSING} = T_{HOUSING}(t(i-1)) + 1/C_{HOUSING} * Q_{HOUSING} * (t(i) - t(i-1))$$

where:

$$Q_{HOUSING} = Q_{BOARD} - Q_{BODY},$$

$$Q_{BOARD} = \frac{(T_{BOARD} - T_{HOUSING}(t(i-1)))}{R_{BOARD}}, \text{ and}$$

$$Q_{BODY} = \frac{(T_{HOUSING}(t(i-1)) - T_{BODY})}{R_{BODY}}.$$

In some examples, IMD 14 and/or external charging device 22 may store values for constants determined for a temperature sensor or for each temperature sensor of IMD 14. In an illustrative example, constant values that may be used in the temperature estimation algorithm include:

$R_{BODY}$~25 K/W (Thermal Resistance to body of patient 12)

$R_{BOARD}$~5 K/W (Thermal Resistance between sensor 39 on circuit board and housing 19)

$C_{HOUSING}$~75 J/K (Heat capacity of housing 19 made from, as an example, a particular titanium alloy)

$T_{BODY}$=37° C.

$T_{HOUSING\_initial} = T_{BOARD\_initial}$.

Figure 7:
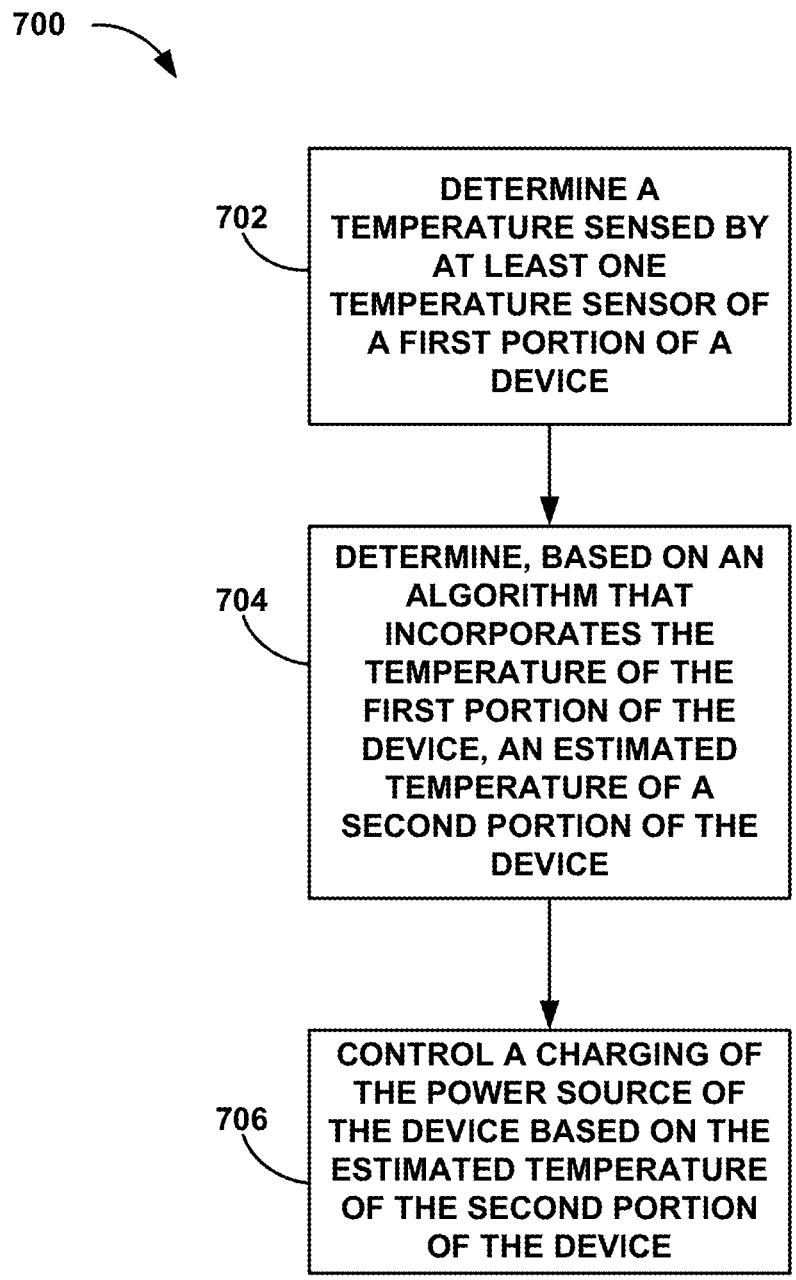
FIG. 7 is a flow diagram that illustrates an example technique for determining an estimated temperature for an example IMD, in accordance with one or more of the various techniques disclosed herein.

FIG. 7 is a flow diagram 700 illustrating an example method of utilizing temperature estimation techniques, in accordance with one or more techniques of this disclosure. The temperature estimation techniques of this disclosure may be used to estimate the temperature of an external portion of the exterior surface of housing 19. In some examples, the example temperature estimation techniques may be as described with reference to any of the figures of this disclosure.

In some examples, processing circuitry, e.g., processing circuitry 30 of IMD 14, or processing circuitry 50 of external charging device 22, may determine a temperature sensed by at least one temperature sensor 39 of a first portion of IMD 14 (702). Next, processing circuitry, e.g., processing circuitry 30 of IMD 14, or processing circuitry 50 of external charging device 22, may determine, based on an algorithm that incorporates the temperature of the first portion of the device, an estimated temperature of a second portion of the device (704). For example, the algorithm may be representative of an estimated temperature difference between the first and second portions of the device based on a dynamic transfer function that operates in a time-domain. The dynamic transfer function may be a first order transfer function. The dynamic transfer function may include a first order low-pass filter. Next, processing circuitry, e.g., processing circuitry 30 of IMD 14, or processing circuitry 50 of external charging device 22, may control a charging of the power source of the device based on the estimated temperature of the second portion of the device (706).

In some instances, processing circuitry 30 and/or processing circuitry 50 may generate an alert at the onset of an abnormal temperature reading. In an example, processing circuitry 50 may generate an alert when the temperature estimated for an external portion of housing 19 exceeds a temperature level threshold for a period of time following some remedial action taken by either IMD 14 or external charging device 22 in an effort to reduce the temperature of the external portion of housing 19. The alert may be an audible alert generated by IMD 14 and/or external charging device 22, a visual alert generated by external charging device 22, or a tactile alert generated by IMD 14 and/or external charging device 22. Furthermore, the alert may be provided to other devices, such as via a computing network.

Temperature sensor(s) 39 may be disposed anywhere within housing 19. In one example, the temperature sensor may be mounted to a printed circuit board within a housing of the medical device (e.g. charging head 26, housing 24, or IMD 14). From the location on the printed circuit board, the temperature sensor may be oriented to sense the temperature of a desired portion of the device (e.g., using infrared sensing, phosphor thermometry, or pressure sensing, etc.). In some examples, this portion to be sensed may be a part of a recharge coil or other components within the medical device (e.g., IMD 14 or external charging device 22). In some examples, the temperature sensor may be mounted to a hybrid board or a separate mounting platform within the device such as disposed on a flexible printed circuit. System 10 may utilize one or more non-thermally coupled temperature sensors in one or more medical device.

The system can use a transfer function between heat input and temperature output and a close relationship can be developed using a second order transfer function (low pass filter). The second order transfer function may include a one-time constant on the order of 5 minutes and another time constant on the order of 20-30 minutes in one example, but other constants may be used in other examples.

In the example illustrated in FIG. 7, processing circuitry 30 is configured to perform the various techniques described herein. To avoid confusion, processing circuitry 30 is described as performing the various processing techniques proscribed to IMD 14, but it should be understood that at least some of these techniques may also be performed by other processing circuitry (e.g., processing circuitry 50 of external charging device 22, processing circuitry of an external server, etc.). In an illustrative example, processing circuitry 50 may receive, via telemetry circuitry 56, temperature measurements from IMD 14, and estimate a temperature of the outside surface of IMD 14 based on the received temperature measurements. Processing circuitry 50 may then control the manner in which electrical current energizes primary coil 48 in order to maintain the estimated temperature of the external portion of housing 19 within a particular temperature range.

Figure 8:
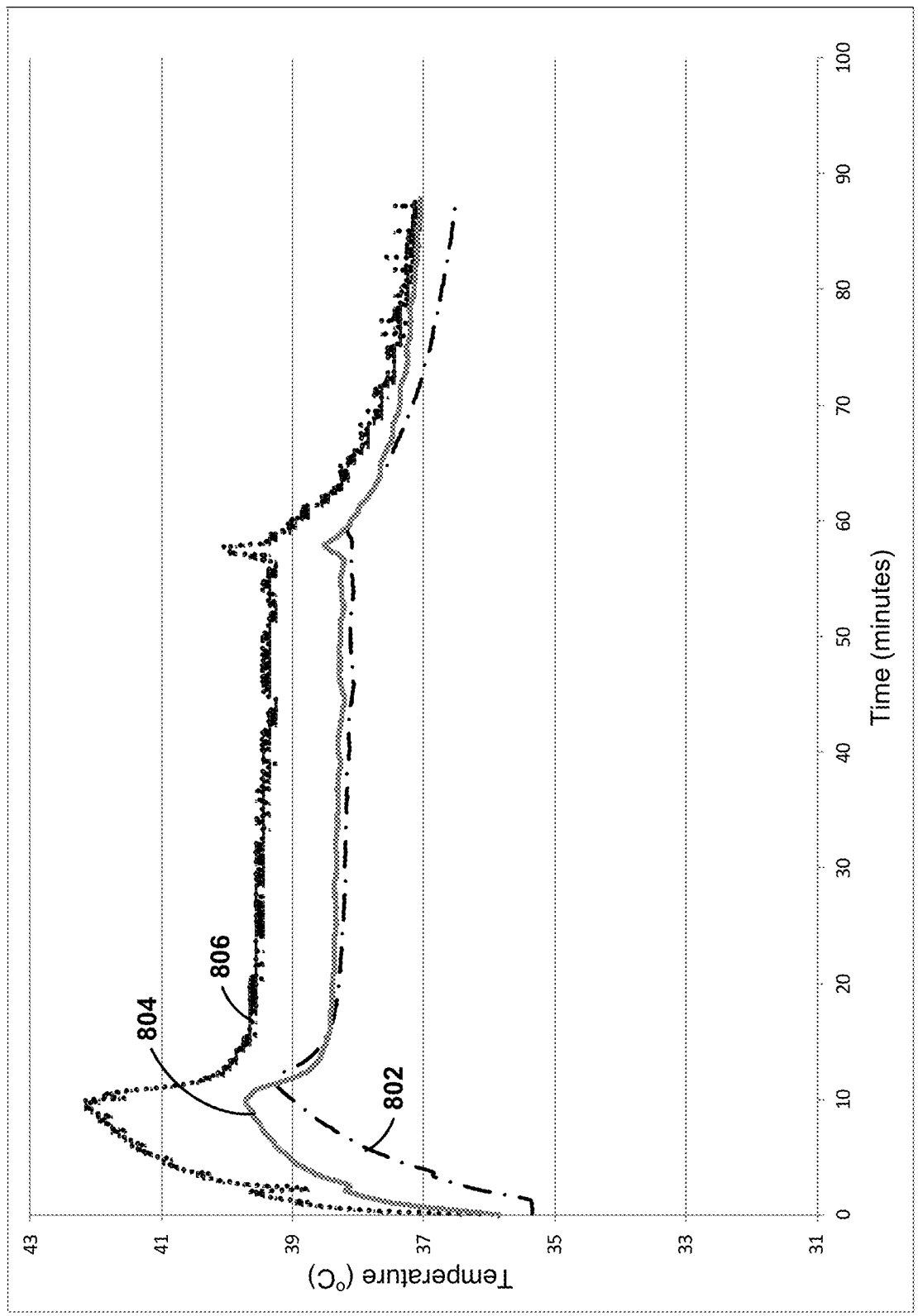
FIG. 8 is a graph of example temperatures generated during an IMD charging process over a period of time, in accordance with one or more of the various techniques disclosed herein.

FIG. 8 is a graph illustrating the correlation between temperatures sensed within the device as achieved via the dynamic transfer function. As shown in the example of FIG. 8, trace 802 represents the actual temperature of the external portion of housing 19. Trace 802 may be determined from an experimental setup at which the actual temperature of housing 19 can be provided to indicate the difference from the internal measured temperature. Trace 806 is the measured temperature T(t) from sensor 80 disposed on board 74. For a system operating within the patient, trace 806 may be the measured temperature available to IMD 14. Trace 804 represents the calculated temperature of housing 19 according to a dynamic transfer function described herein. As can be seen from FIG. 8, the calculated temperature of housing 19 shown by trace 804 approximates the actual temperature of housing 19 in trace 802, which indicates that the dynamic transfer function approximates the housing 19 temperature from the measured temperature on the location of board 74.

Figure 9:
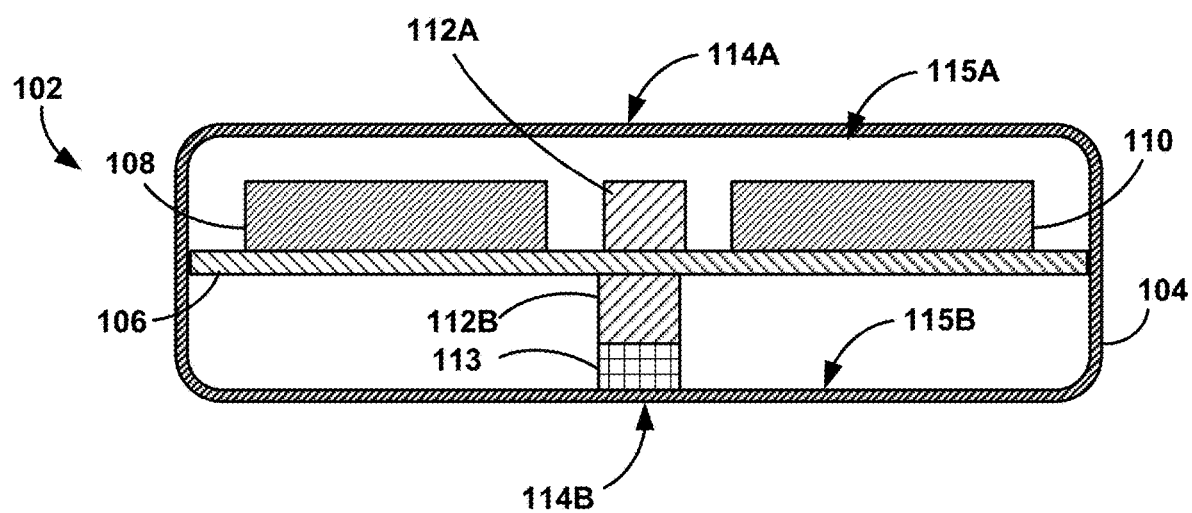
FIG. 9 is a conceptual cross-sectional diagram illustrating example temperature sensors disposed within an example IMD, in accordance with one or more of the various techniques disclosed herein.

FIG. 9 is a conceptual cross-sectional diagram illustrating example temperature sensors 112A-B disposed within an example IMD 102, in accordance with one or more of the various techniques disclosed herein. IMD 102 may be an example of IMD 14 and temperature sensors 112A-B may be an example of temperature sensor(s) 39. The IMD described with reference to FIG. 9 is generally shown with a rectangular cross-section. However, temperature sensors 112A-B may be disposed within an IMD, or any other device, of any size (e.g., shape, weight, etc.).

As shown in FIG. 9, IMD 102 includes housing 104 that includes exterior surfaces 114A-B (collectively "exterior surface 114") and interior surfaces 115A-B (collectively "interior surface 115). Housing 104 encloses circuit board 106, which may be for example a printed circuit board or a hybrid attached to the printed circuit board, electronic circuits 108 and 110, and temperature sensors 112A and 112B (collectively "temperature sensors 112"). Circuit board 106 may be mounted or secured within housing 104. Electronic circuits 108, 110 are mounted to circuit board 106, or to hybrid circuit board(s) mounted to circuit board 106. Electronic circuits 108 and 110 may include various components such as a processing circuitry, memory, and associated circuitry such as any of the circuitry shown in FIG. 2 included in IMD 14. Although not shown in FIG. 9, a secondary coil and power source may also be disposed within housing 104.

As shown in FIG. 9, temperature sensors 112 may be mounted onto opposite sides of circuit board 106. In various examples, temperature sensors 112 are not directly thermally coupled to housing 104, and are not configured to sense a temperature of the housing 104 or the exterior surfaces 114 of IMD 102. Although temperature sensors 112 are illustrated in FIG. 9 as being physically separated from electronic circuits 108, 110, in some examples one or more of temperature sensors 112 may be directly physically coupled to, or for example built into, one or both of electronic circuits 108 and/or 110.

In some examples, sensing the temperature on opposing sides of the circuit board 106 of IMD 102 may be beneficial if IMD 102 becomes flipped within the tissue pocket containing IMD 102 within patient 12. In other words, IMD 102 may be configured to determine that a flip has occurred and/or measure the temperature of a desired surface 114A, 114B of housing 104 regardless of whether IMD 102 has flipped within patient 12. In some examples, the differences in temperatures of surfaces 114A, 114B (e.g., surfaces 114A and 114B are on opposing sides of IMD 102) may be negligible due to the thermal conductance of the material used to form housing 104, particularly for smaller devices (e.g., less than 3 cubic centimeters). In such examples, temperatures estimated for housing 104 based on sensed temperatures provided by either of temperature sensors 112A or 112B would be equally useful in determining the temperature of the exterior surfaces 114 of housing 104 using the techniques, and any equivalents thereof, as described in this disclosure. For example, temperature sensor 112A may be configured to sense a temperature of electronic circuits 108, 110, and temperature sensor 112B may be configured to sense a temperature of circuit board 106. However, larger devices may have non-negligible differences in temperature between different sides of the device.

In some examples, more than one of temperatures sensors 112A, 112B are used at the same time for temperature sensing. In such examples, sensed temperatures may be combined to produce a single value for the temperature provided by temperature sensors 112. This single value may be processed according to the algorithm(s) described in this disclosure (e.g., a dynamic transfer function), and any equivalents thereof, to estimate a temperature, or a series of temperatures over time, of the housing 104 and/or exterior surfaces 114A, 114B of IMD 102. In other examples, each sensed temperature provided individually by sensors 112A, 112B may be provided separately for individual processing to estimate a temperature, or a series of temperatures over time, of the housing 104 and/or exterior surface 114 of IMD 102. The estimated temperatures and/or the series of estimated temperatures may be used to control a charging process being performed on IMD 102.

In some examples, one temperature sensor 112 could be placed on one side of circuit board 106 and another temperature sensor 112 on the other side of circuit board 106. Normally, these will be within +/−1 or +/−3 degrees of each other. In an example, if they are off by some larger amount such as 5 degrees, the system could declare a fault. Similarly, external charging device 22 may compute the estimated temperature of housing 104 for a plurality of temperature spots on the exterior surface of housing 104. If one of temperature sensors 112 is closer to header 26, the temperature sensor 112 may have a slightly different transfer function than the one on the opposite side of IMD 102. Furthermore, the system could detect if more heat is being generated in the header (or one side of the housing 104 based upon the difference between two or more temperature sensors and adjust the transfer function(s) accordingly.

Alternatively, a plurality of temperature sensors 112 may be oriented to sense temperature of different surfaces and/or components within IMD 102. A first temperature sensor 112 may be configured to sense a first internal portion of the device and a second temperature sensor may be configured to sense a second internal portion of IMD 102. The two internal portions may be of different components or different areas of the same component. In one example, the first portion may be one housing surface within the device, and the second portion may be another housing surface within the device. Since temperatures within a device may be non-uniform due to component location, thermal transfer within the device, or other external factors, the multiple temperature sensors may be used to identify temperature variations or "hot spots" of the device. In some cases, a one or multi-dimension array of temperature sensors 112 may be provided to sense one or more internal portions of IMD 102.

In a symmetric design, IMD 102 may need symmetric sensors 112 on the front and back side of 1 MB 102. These additional sensors 112 can be connected to the same or separate communication lines and the faults or shorts of those communication lines should be considered as part of the functional safety system design.

Various tests were completed with an IMD, such as IMD 102, using temperature sensors mounted within a non-functional surrogate and subjected to various test scenarios. Two of these scenarios were analyzed for their respective thermodynamics and transfer functions. Transfer functions and thermodynamic information were determined for 1 MB 14 having sensors 112 disposed inside. A first example involved the use of a thermal pad 113 (e.g., a Bergquist® thermal pad, etc.) between temperature sensor 112B, mounted on the circuit board inside between temperature sensor 112B and housing 104, which may be used to reduce the thermal resistance between temperature sensor 112B and housing 104. A second example involved no thermal pad as a control.

Both Class A (static) and Class B (dynamic) transfer functions were tested using the IMD surrogate. In addition, a combined transfer function was developed by convolving the Class A and Class B transfer functions: First, processing circuitry 30 or processing circuitry 50 may use an algorithm that includes a dynamic transfer function that operates in the time-domain ("Class B transfer function") to adjust the frequency of thermal energy through 1 MB 14. In some examples, the processing circuitry (e.g., processing circuitry 30 or processing circuitry 50) may scale the results using a static transfer function ("Class A transfer function"). In some examples, a combined transfer function may be used by convolving the Class A transfer function and the Class B transfer function. In some examples, a variety of difference discrete low pass filters may be used as at least part of a transfer function.

In an example, the Class A static transfer function may be expressed as:

$$T_{HOUSING} = K_{HOUSING}(T_{BOARD} - T_{offset\_BOARD}) + T_{offset\_BOARD},$$

where K may be the gain of the filter that ends up being used for scaling purposes.

Table 1 below shows how different systems may be more amenable to Class A transfer functions and how other systems may be more amenable to Class A and/or Class B transfer functions. Other features to Table 1 may also be provided in some examples, such as the heat capacity of the object with the temperature sensor, the resistance of the board to the housing, and/or the time constant for the housing. Generally, as the resistances and time constants get larger, class B transfer functions may be more appropriate.

TABLE 1

| System Type | Thermal Resistance to Housing | Transfer Function | Comments regarding use |
|---|---|---|---|
| 1 | Relatively Low | Class A Transfer Function $T_{HOUSING} = K_{HOUSING}(T_{BOARD} - T_{offset\_BOARD}) + T_{offset\_BOARD}$ | $K_{HOUSING} > 1$: $T_{HOUSING} > T_{BOARD}$ $K_{HOUSING} = 1$: $T_{HOUSING} = T_{BOARD}$ $K_{HOUSING} < 1$: $T_{HOUSING} < T_{BOARD}$ |
| 2 | Relatively High | Class B Transfer Function $T_{HOUSING} = T_{HOUSING}(t(i-1)) + 1/C_{HOUSING} * Q_{HOUSING} * [t(i) - t(i-1)]$ Where: $Q_{HOUSING} = Q_{BOARD} - Q_{BODY}$, $Q_{BOARD} = (T_{BOARD} - T_{HOUSING})/R_{BOARD}$, $Q_{BODY} = (T_{HOUSING} - T_{BODY})/R_{BODY}$ | Works when circuit board has higher frequency thermal energy than housing 19 |

TABLE 1-continued

| System Type | Thermal Resistance to Housing | Transfer Function | Comments regarding use |
|---|---|---|---|
| 3 | Relatively Low | Class B Transfer Function<br>$T_{HOUSING} = T_{HOUSING}(t(i-1)) + 1/C_{HOUSING} * Q_{HOUSING} * [t(i) - t(i-1)]$<br>Where:<br>$Q_{HOUSING} = Q_{BOARD} - Q_{BODY}$,<br>$Q_{BOARD} = (T_{BOARD} - T_{HOUSING})/R_{BOARD}$,<br>$Q_{BODY} = (T_{HOUSING} - T_{BODY})/R_{BODY}$ | Works when circuit board has higher frequency thermal energy than housing 19 |

In the example of FIG. 9, the delta in temperature between temperature sensor 112 and an external portion of housing 19 may be greater (on the order of 0.5° C. to 0.6° C.). Here, miniaturization of IMDs requires higher temperature control accuracy, but the discrepancy between the sensor temperature and external housing temperature may be less in magnitude.

Figure 10:
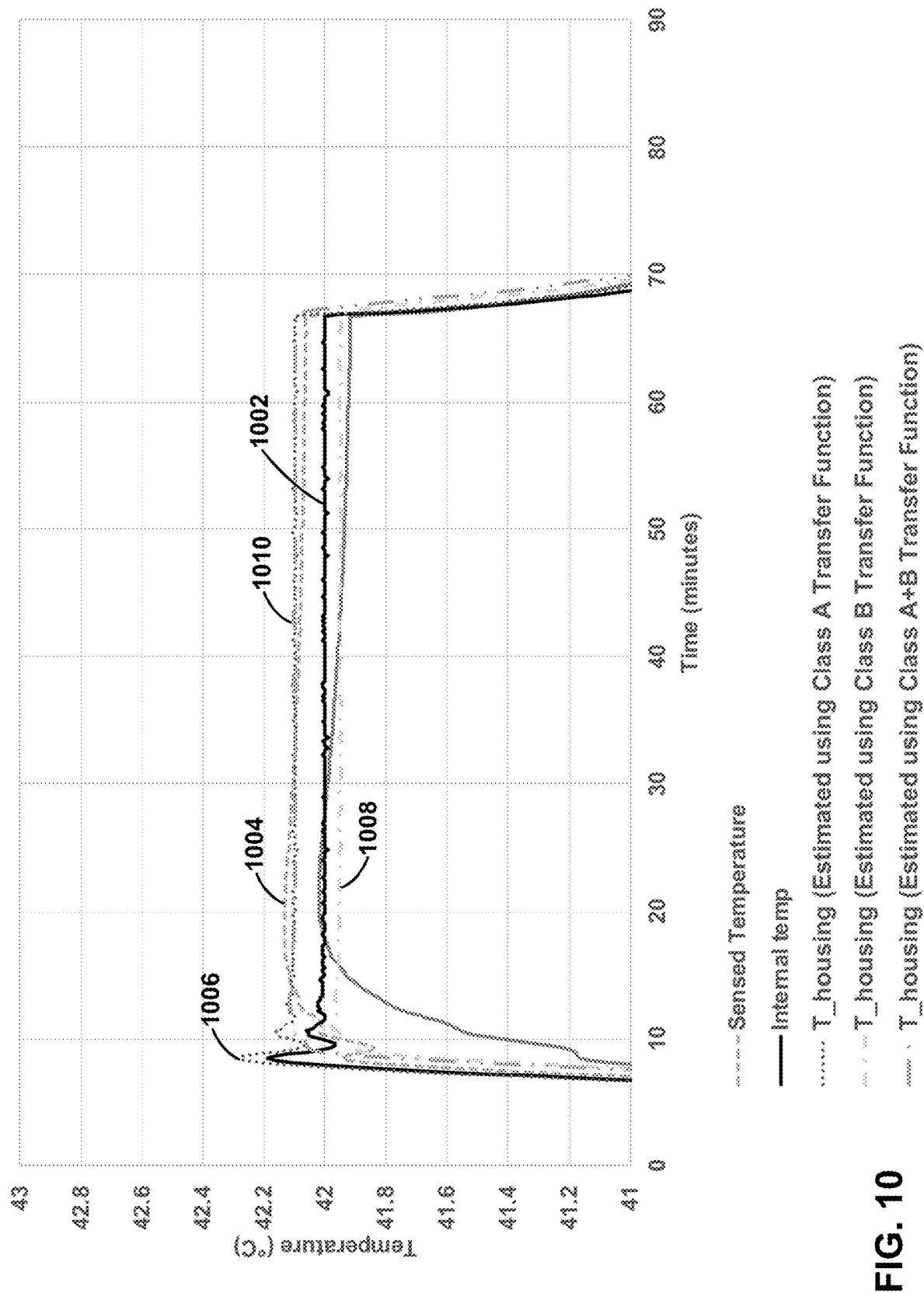
FIG. 10 is a graph of example temperatures generated during an IMD charging process over a period of time, in accordance with one or more of the various techniques disclosed herein.

FIG. 10 is a graph illustrating temperature estimations with a thermal pad 113. As shown in FIG. 10, measured temperatures are compared with estimated temperatures based on different transfer functions. Trace 1002 represents the measured internal temperature of the temperature on the board of IMD 14, and trace 1004 represents what the actual temperature of the external portion of housing 19 would be. Trace 1006 represents the estimated temperature of housing 19 using a Class A transfer function, and trace 1008 represents the estimated temperature of housing 19 using a Class B transfer function. Trace 1010 represents the estimated temperature of housing 19 when using a combination of the Class A and Class B transfer functions.

In some examples, a static transfer function may initially overestimate the temperature of housing 19 (using $K_{HOUSING} > 1$), such as shown in trace 1006 of FIG. 10. Trace 1008 of FIG. 10 may represent the result of the Class B transfer function (low pass filter). However, the dynamic transfer function alone may underestimate the temperature of housing 19 in certain situations as shown when comparing trace 1008 to the actual temperature of housing 19 by trace 1004. In such instances, such as when thermal pad 113 provides a thermal connection between the temperature sensor and housing 19, a combination Class A and Class B transfer function may be used as shown by trace 1010 of FIG. 10 in comparison to the actual sensed temperature of housing 19 indicated by trace 1004.

Figure 11:
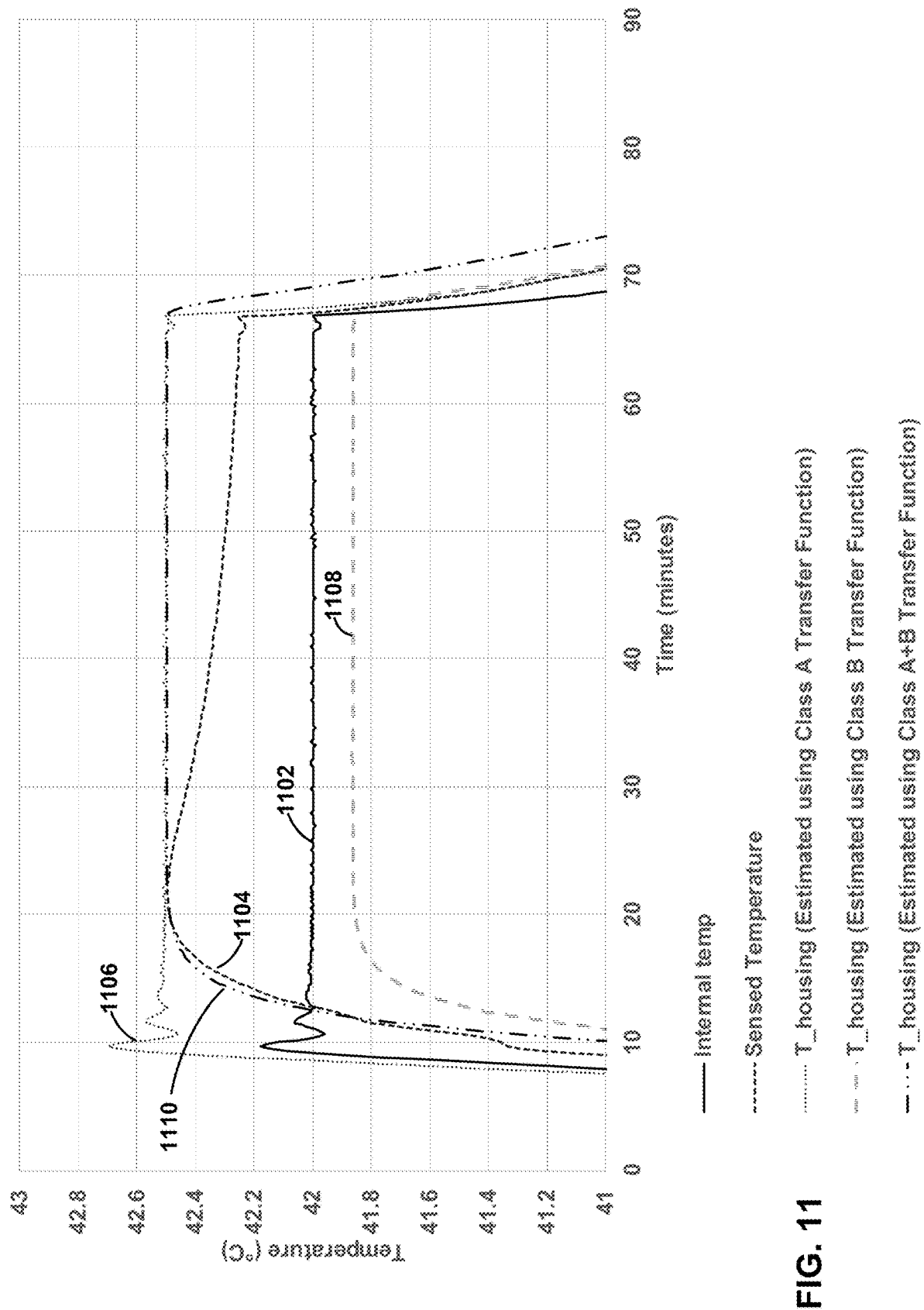
FIG. 11 is a graph of example temperatures generated during an IMD charging process over a period of time, in accordance with one or more of the various techniques disclosed herein.

FIG. 11 is a graph illustrating the accuracy of estimating the temperature of an external portion of housing 19 of IMD 14 using a dynamic transfer function, a static transfer function, and a combination of a dynamic transfer function and static transfer function for temperature sensor 39, in accordance with one or more of the various techniques disclosed herein. In this example, temperature sensor 39 does not include a thermal management element, such as a thermal pad, to alter the thermal resistance of IMD 14. Instead, temperature sensor 39 may be separated from housing 19 by an air gap (e.g., helium, argon, nitrogen or atmospheric air contained within housing 19).

Line 1102 represents the temperature reading obtained from temperature sensor(s) 39 disposed within IMD 14. In some examples, the temperature reading may represent a maximum temperature as determined from a plurality of temperature sensors 39. In another example, a temperature estimate may be obtained from a plurality of temperature sensors 39 and then the maximum temperature estimate may be used. That is, line 1102 may represent a maximum temperature reading representative of readings from a plurality of temperature sensors 39 or a single temperature reading obtained from a single temperature sensor 39.

The dashed line 1104 in FIG. 11 is a temperature sensor reading from a temperature sensor attached to an external portion of housing 19 that is used as a comparison with temperature measurements obtained from within IMD 14 from one or more temperature sensor(s) 39. The external temperature sensor is separate and distinct from temperature sensor 39 disposed within IMD 14 and was only used for testing the accuracy of using the transfer functions to estimate the external temperature of housing 19 that coincides with the tester temperature sensor attached to the external portion of housing 19.

In some examples, a dynamic transfer function (Class B) alone as shown by trace 1108 may tend to underestimate the temperature of an external portion of housing 19 (as compared to dashed line 1104. The Class A transfer function shown by trace 1106 is certainly functional and could be used in a real system should this configuration be developed further. However, the temperature of housing 19 (dashed line 1104) does not have all the same high frequency thermal energy as trace 1106 of the Class A transfer function. In some examples, a combination of a Class A transfer function and Class B transfer function, shown as trace 1110, may be used to estimate the temperature of housing 19 since it closely approximates the temperature of housing 19.

As shown in FIG. 11, this test data set, drops off in temperature after 25 minutes. This could be caused by heating of the test bath in which IMD 14 was submerged or some other unknown cause. In any case, the combined Class A and Class B transfer function may be configured to allow processing circuitry 30 or processing circuitry 50 to estimate the temperature of housing 19 to within 0.25° C. based on the sensed temperatures obtained via temperature sensor(s) 112.

Figure 12:
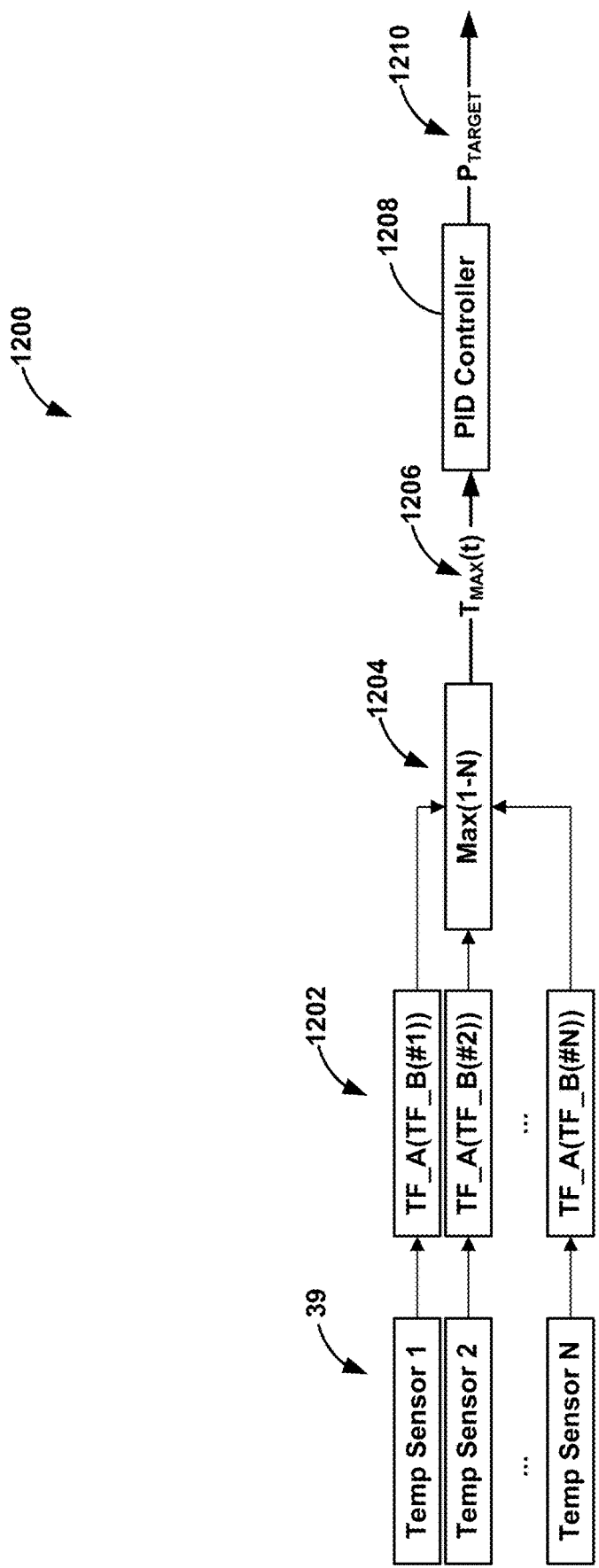
FIG. 12 is a flow diagram that illustrates an example technique for controlling the charging of a power source based on a plurality of estimated temperatures, in accordance with one or more of the various techniques disclosed herein.

FIG. 12 is a block diagram that illustrates an example technique for controlling the charging of power source 18 based on a plurality of estimated temperatures, in accordance with one or more of the various techniques disclosed herein. Each temperature sensor 39 may correspond to a unique transfer function 1202. As shown, each temperature sensor 39 corresponds to a combined transfer function that includes a dynamic transfer function (TF_B) and a static transfer function (TF_A). Other examples of transfer function 1202 include various types of Finite Impulse Response (FIR) or Infinite Impulse Response (IIR) filters. FIR filters may include, for example, a simple moving average of the last N samples. IIR filters on the other hand calculate the next output based on previous output(s) which is a form of feedback. The example given previously for Class B transfer function is an IIR filter. Other IIR or FIR filters could be equally effective. Processing circuitry 30 or processing circuitry 50 may determine the maximum temperature estimated from each temperature sensor 39 (1204). Processing circuitry 30 or processing circuitry 50 may execute PID controls using PID Controller 1208 based on the maximum estimated temperature ($T_{MAX}(t)$) 1206. Based on the PID controls, processing circuitry 30 or processing circuitry 50 may determine a target charging power ($P_{TARGET}$) 1210. An example of PID controls is described with referenced to FIG. 13.

Figure 13:
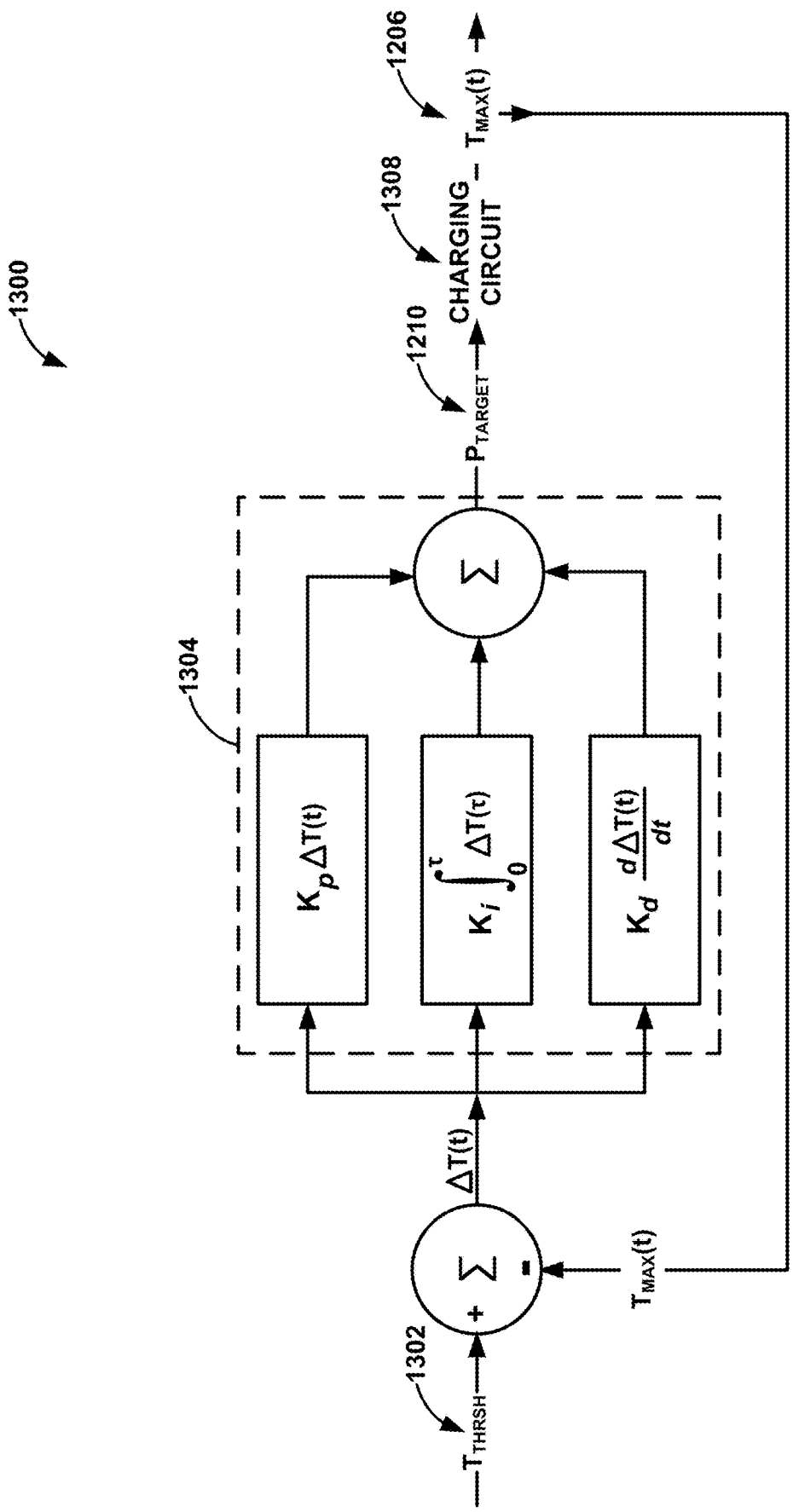
FIG. 13 is a block diagram of an example control system that dynamically determines target charge power levels for the IMD charging process, in accordance with one or more of the various techniques disclosed herein.

FIG. 13 is a block diagram of an example control loop 1300 that dynamically determines target charge power levels for the charging process of IMD 14, in accordance with one or more of the various techniques disclosed herein. In some examples, the control loop 1300 continuously modulates control for the charging process of IMD 14. The control loop 1300 may provide control based on a three-term controller 1304. In an example, the control loop 1300 provides control based on proportional (P), integral (I), and derivative (D) terms that utilize a maximum estimated temperature obtained via temperature sensor(s) 39 to determine a target charging power level 1306 for commanding a charging circuit 1308 (e.g., charging circuitry 38 of IMD 14, charging circuitry 58 of external charging device 22) during the charging process of IMD 14 to then output a target amount of power based on the temperature estimated for housing 19 (e.g., $T_{max}$ at a current time (t)). FIG. 13 illustrates the principles for how the PID terms of a PID controller are applied to determine the target charging power ($P_{power}$). T(t) is the measured process value and ΔT(t) represents the difference between a desired setpoint 1302 ($T_{thrsh}$ for temperature level threshold) and a temperature estimate as determined from determining the maximum estimated temperature 1206 from a plurality of temperature sensors 39.

In some instances, control loop 1300 may instead include a one-term controller or a two-term controller. In any case, a temperature-controlled approach that utilizes estimated temperatures of the external portions of housing 19 may be more accurate than a heat-controlled (conservation of energy) control algorithm. This has been demonstrated in at least some instances based on empirical data where both approaches were tested simultaneously to determine which would be more advantageous for implementing in the charging process of IMD 14.

Figure 14:
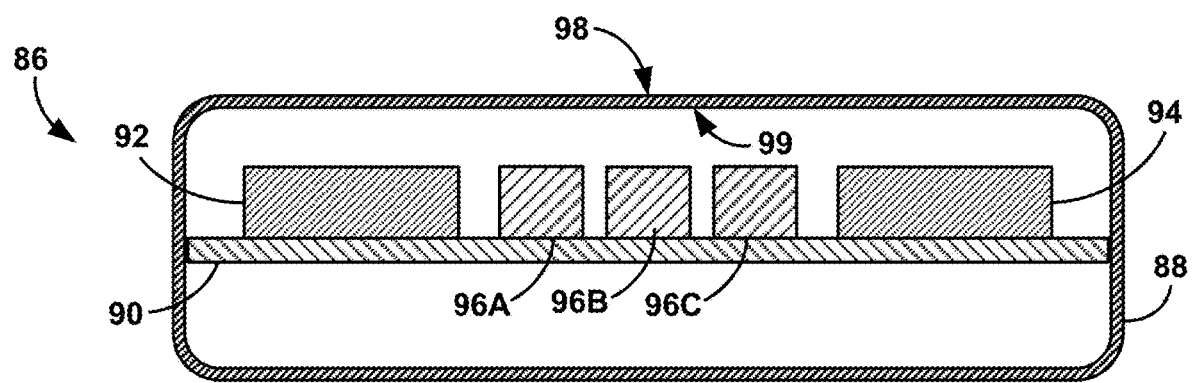
FIG. 14 is a conceptual cross-sectional diagram illustrating an example of temperature sensors disposed within an IMD, in accordance with one or more of the various techniques disclosed herein.

FIG. 14 is a conceptual cross-sectional diagram illustrating an example of temperature sensors 96A-C disposed within an example IMD 86, in accordance with one or more of the various techniques disclosed herein. IMD 86 may be an example of IMD 14 and temperature sensors 96A-C may be an example of temperature sensor(s) 39. The IMD described with reference to FIG. 14 is generally shown with a rectangular cross-section. However, temperature sensors 96A-C may be disposed within an IMD, or any other device, of any size (e.g., shape, weight, etc.).

As shown in FIG. 14, 1 MB 86 includes housing 88 that includes exterior surface 98 and interior surface 99. Housing 88 encloses circuit board 90, which may be for example a printed circuit board or a hybrid attached to the printed circuit board, electronic circuits 92 and 94, and temperature sensors 96A, 96B, and 96C (collectively "temperature sensors 96"). Circuit board 90 may be mounted or secured within housing 88. Electronic circuits 92, 94 are mounted to circuit board 90, or comprise hybrid circuit boards mounted to circuit board 90. Electronic circuits 92 and 94 may include various components such as a processing circuitry, memory, and associated circuitry, such as any of the circuitry shown in FIG. 2 included in 1 MB 14. Although not shown in FIG. 14, a secondary coil and power source may also be disposed within housing 88.

In some examples, temperature sensors 96 may be mounted onto a surface of circuit board 90. In addition, or alternatively, one or more of temperature sensors 96 may not be directly thermally coupled to housing 88, and are not configured to directly sense a temperature of housing 88 or the exterior surface 98 of IMD 86. Although temperature sensors 96 are illustrated in FIG. 14 as being physically separated from electronic circuits 92, 94, in some examples, one or more of temperature sensors 96 may be directly physically coupled to, or for example built into, one or both of electronic circuits 92 and/or 94.

Temperature sensors 96 are not limited to any particular type of temperature sensor, and may be for example one or some combination of a thermistor, a thermocouple, a resistance thermometer, and/or a silicon bandgap temperature sensor. In some examples, temperature sensors 96 may include multiple temperature sensors configured to sense a temperature or different temperatures associated with circuit board 90 and/or electronic circuits 92, 94. For example, temperature sensor 96A may be configured to sense a temperature of electronic circuit 92, temperature sensor 96B may be configured to sense a temperature of circuit board 90, and temperature sensor 96C may be configured to sense a temperature of electronic circuit 94. In some examples, more than one of temperatures sensors 96A, 96B and 96C are used at a same time for temperature sensing. In some examples, the difference in temperatures between different sensors may be used to adjust the K of the housing, the resistance of the board and/or the resistance of the body. Temperatures sensed via temperature sensors 96A-C may be combined (e.g., averaged) to produce a single value for the temperature provided by temperature sensors 96. This single value may be processed according to the algorithm(s) described in this disclosure, and any equivalents thereof, to estimate a temperature, or a series of temperatures over time, of housing 88 and/or exterior surface 98 of IMD 86. In other examples, each sensed temperature provided individually by sensors 96A, 96B, and 96C may be provided separately for individual processing to estimate a temperature, or a series of temperatures over time, of housing 88 and/or exterior surface 98 of IMD 86. The multiple sets of estimated temperatures and/or the series of estimated temperatures may be used to control a charging process being performed on IMD 86.

Figure 15:
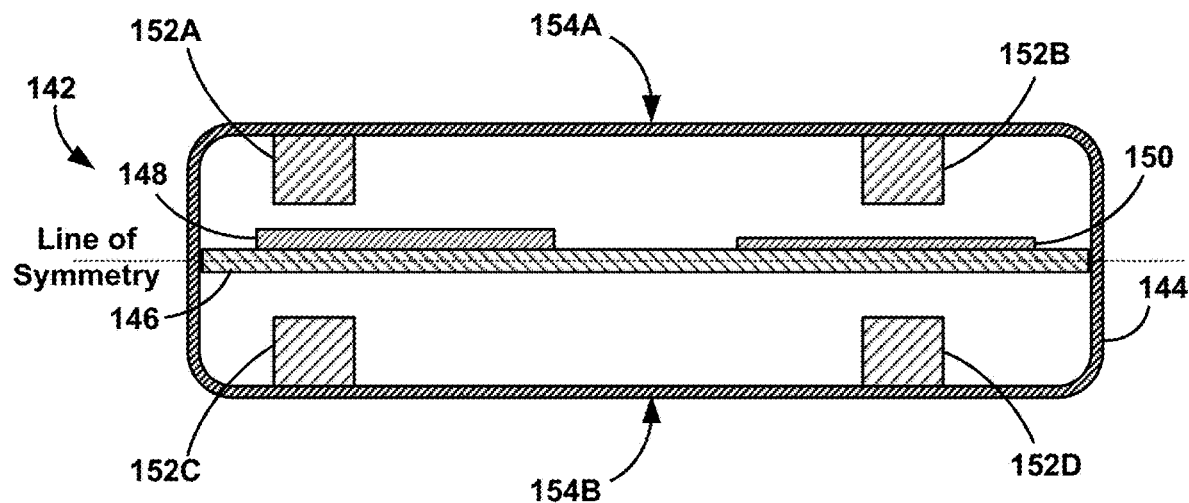
FIG. 15 is a conceptual cross-sectional diagram illustrating an example of temperature sensors disposed within an IMD, in accordance with one or more of the various techniques disclosed herein.

FIG. 15 is a conceptual cross-sectional diagram illustrating an example of temperature sensors 152A-D disposed within an example IMD 142, in accordance with one or more of the various techniques disclosed herein. IMD 142 may be an example of IMD 14 and temperature sensors 152A-D may be an example of temperature sensor(s) 39. The IMD described with reference to FIG. 15 is generally shown with a rectangular cross-section. However, temperature sensors 152A-D may be disposed within an IMD, or any other device, of any size (e.g., shape, weight, etc.). In some instances, instead of being a part of the interior surface of the housing, temperature sensors 152A-D may be, in some examples, be connected to board 146.

A subset of temperature sensors 152A-D may be used to determine the temperatures of the closest various portions of IMD 142, such as surface 154A, surface 154B, surface 144, electrical components 148, or electrical components 150. For example, 1 MB 142 may estimate the temperature of surface 154A based on the measured temperatures of temperature sensors 152A and 152B. In any case, the same algorithmic principles could be applied using transfer functions for controlling to the maximum estimated housing 19 temperature of all sensors, as described for a single sensor.

Figure 16:
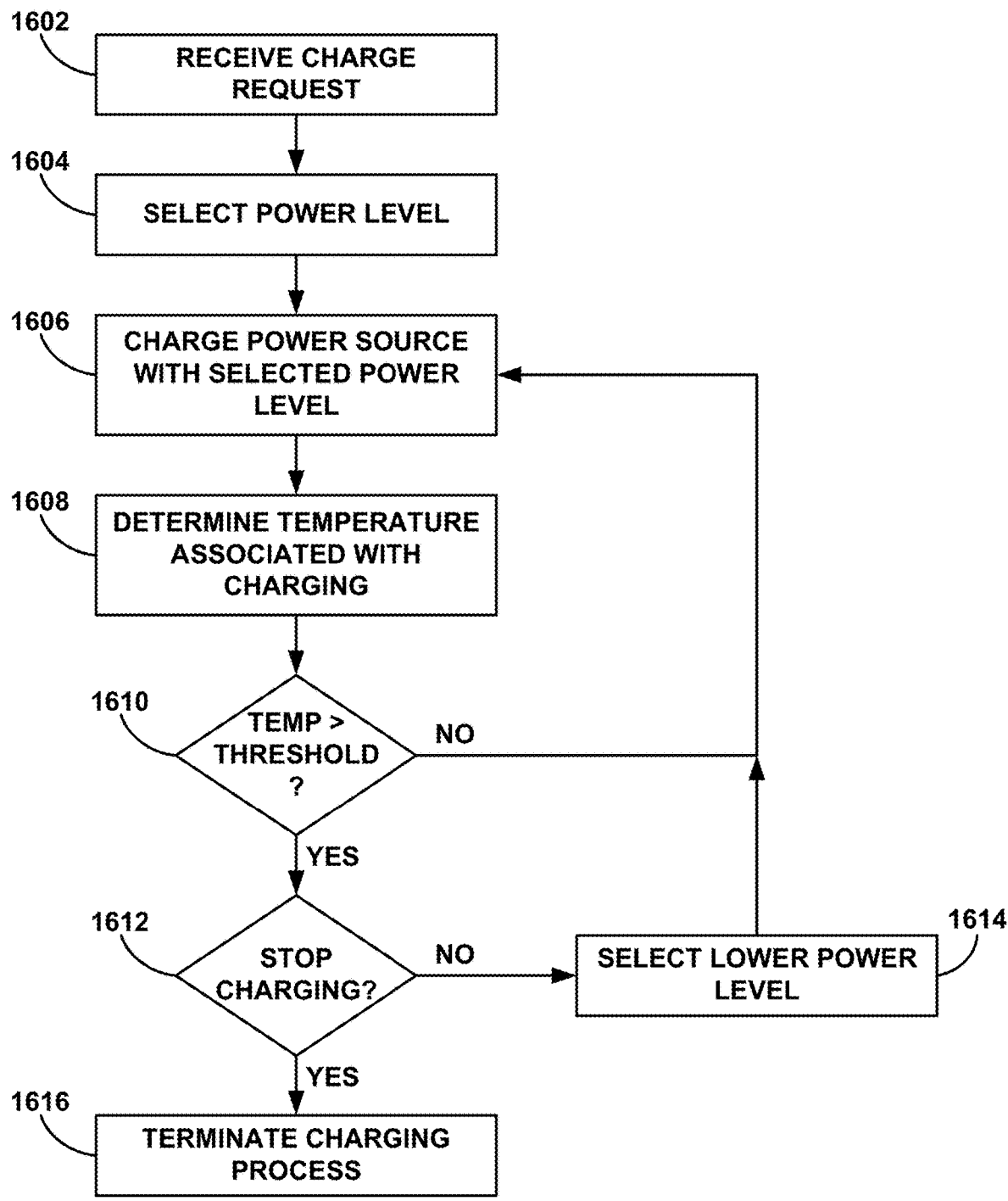
FIG. 16 is a flow diagram that illustrates an example technique for controlling the charging of a power source based on an estimated temperature of an IMD housing, in accordance with one or more of the various techniques disclosed herein.

FIG. 16 is a flow diagram that illustrates an example technique for controlling the charging of power source 18 based on an estimated temperature of housing 19, in accordance with one or more of the various techniques disclosed herein. Although processing circuitry 50 of charging device 22 is described as generally performing the techniques of FIG. 16, the techniques may, in some instances, be performed by processing circuitry 30, processing circuitry 50, or both processing circuitry 30 and processing circuitry 50 in coordination with one another. The techniques of FIG. 16 may be employed to charge devices using temperatures sensed by temperature sensor(s) 39 that are disposed within 1 MB 14 and/or temperature sensor(s) 59 disposed within external charging device 22 that have been adjusted with any one or more of the transfer functions described herein to estimate a different portion of 1 MB 14, such as the temperature of housing 19.

In some examples, processing circuitry (e.g., processing circuitry 30 of 1 MB 14, processing circuitry 50 of external charging device 22) may receive a charge request (1602). In an example, a charging session for power source 18 may begin when processing circuitry 50 receives a charge request. Processing circuitry 50 may select the power level for the charging process of power source 18 (1604). Processing circuitry 50 may then control charging device 22 to charge power source 18 with the selected power level (1606). During the charging process, temperature sensor(s) 39 may determine the temperature of an internal portion of 1 MB 14 (1608). Processing circuitry 30 may transmit the determined temperatures to charging device 22. Processing circuitry 50 may determine an estimated temperature of housing 19 of IMD 14 based on the temperature received from IMD 14 (e.g., by applying one or more dynamic transfer functions to the measured temperature). In other examples, processing circuitry 30 of IMD 14 may determine the estimated temperature and transmit the estimated temperature or transmit a command to external charging device 22. As long as the estimated temperature remains below or equal to a predetermined temperature level threshold ("NO" branch of block 1610), processing circuitry 50 may continue to charge power source 18 with the selected power level (back to 1606).

In response to the estimated temperature becoming greater than the temperature level threshold ("YES" branch of block 1610), processing circuitry 50 may determine if charging is to stop (1612). In an example, processing circuitry 50 may have received a stop charging command from the user, power source 18 may be fully recharged, or the charging process may be stopped for any other reason. If processing circuitry 50 is not to stop charging ("NO" branch of block 1612), processing circuitry 50 may select a lower power level (1614) and continue to charge power source 18 using the lower power level. This lower level may be a trickle charge, a cycled (on/off) charge or other power level that IMD 14 or external charging device 22 determines will likely not increase the temperature of charging head 26 or housing 19 above a temperature level threshold. If processing circuitry 50 determines that the charging session is to be stopped ("YES" branch of block 1612), processing circuitry 50 may terminate the charging process (1616).

In this manner, processing circuitry 50 may control the charging of power source 18 based on the sensed temperatures from one or more non-thermally coupled temperature sensor. In the case of multiple temperatures, processing circuitry 50 may control the charging based on the temperature sensor outputting the highest temperatures. In other examples, processing circuitry 50 may average or otherwise generate an overall temperature based on the multiple temperature measurements.

While described from the perspective of IMD 14 and components of IMD 14 performing one or more of the various techniques disclosed herein in some instances, it should be noted that system 10 of this disclosure supports bidirectional communication between IMD 14 and external charging device 22. As such, processing circuitry 50 of external charging device 22 may determine a temperature estimate for an external portion of housing 19, similar to the way in which IMD 14 may determine a temperature estimate for an external portion of housing 19. In an example, IMD 14 may communicate temperature data sensed via temperature sensor(s) 39 to external charging device 22. External charging device 22 may determine an estimated temperature of the external portion of housing 19 based on an algorithm that incorporates the sensed temperature data.

In addition, external charging device 22 may utilize temperature data sensed via temperature sensor(s) 59, in conjunction with temperature data sensed to estimate the temperature of an external portion of housing 19. For example, if charging device 22 is placed against the skin of the patient, heat from charging device 22 may increase the temperature of the skin of the patient which may in turn increase the temperature of the tissue surrounding housing 19. As such, to estimate the temperature of housing 19, charging device 22 or IMD 14 may adjust the estimated temperature using a transfer function based on the temperature of charging device 22. As system 10 supports bidirectional communication between IMD 14 and external charging device 22, external charging device 22 may similarly communicate temperature data sensed via temperature sensor(s) 59 to IMD 14. As such, IMD 14 may also utilize temperature data sensed via temperature sensor(s) 59, in conjunction with temperature data sensed via temperature sensor(s) 39 to estimate the temperature of an external portion of housing 19 of IMD 14.

It should also be understood that, in some instances a third device or several devices (e.g., routers, remote servers, etc.) may interface with one or more of IMD 14 and external charging device 22 to communicate data between IMD 14 and external charging device 22 or to receive data from IMD 14 and/or external charging device 22, including sensed temperature measurements and/or estimated temperatures, and estimate the temperature of an external portion of housing 19 based on the received communications. In another example, the third device or combination of other devices may transmit the estimated temperature to IMD 14 and/or external charging device 22 for further processing and controls analysis. In some instances, the other device(s) may convey instructions configured to cause an adjustment to the charging process based on the estimated temperature of housing 19.

The follow examples are described herein. Example 1: A method comprising: determining, via at least one temperature sensor, a temperature of a first portion of a device during a charging process of a power source of the device; estimating, by processing circuitry and based on an algorithm that incorporates the temperature of the first portion of the device, a temperature of a second portion of the device, wherein the algorithm is representative of an estimated temperature difference between the first portion of the device and the second portion of the device based at least in part on a dynamic transfer function that operates in a time-domain; and controlling, by the processing circuitry and based on the temperature of the second portion of the device, charging of the power source.

Example 2: The method of example 1, wherein the device comprises an implantable medical device.

Example 3: The method of any of examples 1 or 2, wherein the dynamic transfer function is expressed as:

$$T_1(t(i)) = T_1\left((t(i-1)) + \frac{1}{C_1} * Q_1[t(i)] - \frac{1}{C_1} * Q_1[t(i-1)]\right),$$

wherein
$T_1(t(i))$=an estimated temperature of the second portion of the device at a first time,
$T_1(t(i-1))$=an estimated temperature of the second portion of the device obtained via a previous iteration of the algorithm,
$C_1$=heat capacity of the second portion of the device,
$Q_1(t(i))$=an estimated amount of heat absorption at the second portion of the device at the first time, and
$Q_1(t(i-1))$=an estimated amount of heat absorption at the second portion of the device obtained via the previous iteration of the algorithm.

Example 4: The method of any of examples 1 through 3, wherein the dynamic transfer function is implemented using a first order low-pass filter.

Example 5: The method of example 4, wherein the algorithm is representative of the estimated temperature difference between the first portion of the device and the second portion of the device based on a static transfer function and the dynamic transfer function.

Example 6: The method of example 5, wherein the algorithm is representative of the estimated temperature difference between the first portion of the device and the second portion of the device based on a static transfer function and the dynamic transfer function when the device has a thermal resistance between the at least one temperature sensor and the second portion of the device that exceeds a thermal resistance threshold.

Example 7: The method of any of examples 1 through 6, wherein the device includes a plurality of temperature sensors including the at least one temperature sensor, wherein estimating the temperature of the second portion of the device further comprises: receiving a temperature value from each of the plurality of temperature sensors; identifying, from the temperature values received from the plurality of temperature sensors, a temperature value that is greater than the other temperature values obtained via the plurality of temperature sensors; and estimating, based on the dynamic transfer function, the temperature of at least one spot on the second portion of the device based at least in part on the temperature values received from each of the plurality of temperature sensors.

Example 8: The method of example 7, wherein controlling charging of the power source comprises: determining a maximum temperature estimate based on the plurality of temperature sensors; and determining a target charging power based on the maximum temperature.

Example 9: The method of any of examples 7 through 8, wherein determining the target charging power includes utilizing a PID control algorithm that incorporates the maximum temperature estimated from the plurality of temperature sensors.

Example 10: The method of any of examples 7 through 9, wherein a first temperature sensor of the plurality of temperature sensors corresponds to a first transfer function, and wherein a second temperature sensor of the plurality of temperature sensors corresponds to a second transfer function, wherein the first transfer function is different than the second transfer function.

Example 11: The method of example 10, wherein the first transfer function is based on a convolution of the dynamic transfer function with a static transfer function.

Example 12: The method of any of examples 1 through 11, wherein the first portion comprises an internal portion of the device, and wherein the second portion comprises an external surface of a housing of the device.

Example 13: The method of any of examples 1 through 12, wherein the at least one temperature sensor is incorporated as part of an integrated circuit located within the first portion of the device.

Example 14: A system comprising: a memory configured to store temperature data obtained via at least one temperature sensor that is disposed within an internal portion of a medical device; and processing circuitry coupled to the memory and configured to: receive the temperature data, the temperature data being indicative of a temperature of the internal portion of the medical device; and determine an estimated temperature of an external surface of a housing of the medical device based on an algorithm that incorporates the temperature data, wherein the algorithm is representative of an estimated temperature difference between the internal portion of the medical device and the external surface of the medical device based at least in part on a dynamic transfer function that operates in a time-domain.

Example 15: The system of example 14, wherein the processing circuitry is further configured to: control charging of a power source of the medical device based on the estimated temperature of the external surface of the housing of the medical device.

Example 16: The system of example 15, wherein the processing circuitry is implemented by an external charging device.

Example 17: The system of any of examples 14 through 16, wherein the dynamic transfer function is based on thermal properties of the housing of the medical device.

Example 18: A non-transitory computer-readable storage medium having stored thereon instructions that, when executed, cause one or more processors to: determine a temperature sensed by at least one temperature sensor of a first portion of a device; determine, based on an algorithm that incorporates the temperature of the first portion of the device, an estimated temperature of a second portion of the device, wherein the algorithm is representative of an estimated temperature difference between the first portion of the device and the second portion of the device based at least in part on a dynamic transfer function that operates in a time-domain; and control a charging of the power source of the device based on the estimated temperature of the second portion of the device.

Example 19: The non-transitory computer-readable storage medium of example 18, wherein the dynamic transfer function is implemented using a low-pass filter.

Example 20: The non-transitory computer-readable storage medium of any of examples 18 and 19, wherein the low-pass filter includes a first order low-pass filter or a second or higher order low-pass filter.

It should be understood that various aspects disclosed herein may be combined in different combinations than the combinations specifically presented in the description and accompanying drawings. It should also be understood that, depending on the example, certain acts or events of any of the processes or methods disclosed herein may be performed in a different sequence, may be added, merged, or left out altogether (e.g., all described acts or events may not be necessary to carry out the disclosed techniques). Moreover, in certain examples, acts or events may be performed concurrently, e.g., through multi-threaded processing, interrupt processing, or multiple processors, rather than sequentially. In addition, while certain aspects of this disclosure are described as being performed by a single module or unit for purposes of clarity, it should be understood that the techniques of this disclosure may be performed by a combination of units or modules associated with, for example, a medical device.

In one or more examples, the disclosed techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more DSPs, general purpose microprocessors, ASICs, FPGAs, CPLDs, or any other equivalent integrated or discrete logic circuitry, or combinations thereof. Accordingly, the term "processing circuitry," as used herein may refer to any of the foregoing structure or any other structure suitable for implementation of the techniques of this disclosure. The disclosed technology may be fully implemented in one or more circuits or logic elements.

One or more of the various techniques disclosed herein may be implemented in a wide variety of devices or apparatuses, including an integrated circuit (IC) or a set of ICs (e.g., a chip set). Various components, modules, or units are described in this disclosure to emphasize functional aspects of devices configured to perform one or more of the various techniques discloses herein, but do not necessarily require realization by different hardware units.

Various examples of the disclosed technology have been described. These and other examples are within the scope of the following claims.

What is claimed is:

1. A method comprising:
   determining, via at least one temperature sensor, a temperature of a first portion of a device during a charging process of a power source of the device;
   estimating, by processing circuitry and using an algorithm that incorporates the temperature of the first portion of the device, a temperature of a second portion of the device, wherein the algorithm is representative of an estimated temperature difference between the first portion of the device and the second portion of the device according to at least a dynamic transfer function that operates in a time-domain, and wherein the dynamic transfer function is implemented using a first order low-pass filter; and
   controlling, by the processing circuitry and based on the temperature of the second portion of the device, charging of the power source.

2. The method of claim 1, wherein the device comprises an implantable medical device.

3. The method of claim 1, wherein the dynamic transfer function is expressed as:

$$T_1(t(i)) = T_1\left((t(i-1)) + \frac{1}{C_1} * Q_1[t(i)] - \frac{1}{C_1} * Q_1[t(i-1)]\right),$$

wherein
   $T_1(t(i))$=an estimated temperature of the second portion of the device at a first time,
   $T_1(t(i-1))$=an estimated temperature of the second portion of the device obtained via a previous iteration of the algorithm,
   $C_1$=heat capacity of the second portion of the device,
   $Q_1(t(i))$=an estimated amount of heat absorption at the second portion of the device at the first time, and
   $Q_1(t(i-1))$=an estimated amount of heat absorption at the second portion of the device obtained via the previous iteration of the algorithm.

4. The method of claim 1, wherein the algorithm is representative of the estimated temperature difference between the first portion of the device and the second portion of the device based on a static transfer function and the dynamic transfer function.

5. The method of claim 4, wherein the algorithm is representative of the estimated temperature difference between the first portion of the device and the second portion of the device based on a static transfer function and the dynamic transfer function when the device has a thermal resistance between the at least one temperature sensor and the second portion of the device that exceeds a thermal resistance threshold.

6. The method of claim 1, wherein the device includes a plurality of temperature sensors including the at least one temperature sensor, wherein estimating the temperature of the second portion of the device further comprises:
   receiving a temperature value from each of the plurality of temperature sensors;
   identifying, from the temperature values received from the plurality of temperature sensors, a temperature value that is greater than the other temperature values obtained via the plurality of temperature sensors; and
   estimating, based on the dynamic transfer function, the temperature of at least one spot on the second portion of the device based at least in part on the temperature values received from each of the plurality of temperature sensors.

7. The method of claim 6, wherein controlling charging of the power source comprises:
   determining a maximum temperature estimate based on the plurality of temperature sensors; and
   determining a target charging power based on the maximum temperature.

8. The method of claim 6, wherein determining the target charging power includes utilizing a PID control algorithm that incorporates the maximum temperature estimated from the plurality of temperature sensors.

9. The method of claim 6, wherein a first temperature sensor of the plurality of temperature sensors corresponds to a first transfer function, and wherein a second temperature sensor of the plurality of temperature sensors corresponds to a second transfer function, wherein the first transfer function is different than the second transfer function.

10. The method of claim 9, wherein the first transfer function is based on a convolution of the dynamic transfer function with a static transfer function.

11. The method of claim 1,
wherein the first portion comprises an internal portion of the device, and
wherein the second portion comprises an external surface of a housing of the device.

12. The method of claim 1, wherein the at least one temperature sensor is incorporated as part of an integrated circuit located within the first portion of the device.

13. A system comprising:
a memory configured to store temperature data obtained via at least one temperature sensor that is disposed within an internal portion of a medical device; and
processing circuitry coupled to the memory and configured to:
receive the temperature data, the temperature data being indicative of a temperature of the internal portion of the medical device; and
determine an estimated temperature of an external surface of a housing of the medical device using an algorithm that incorporates the temperature data, wherein the algorithm is representative of an estimated temperature difference between the internal portion of the medical device and the external surface of the medical device according to at least a dynamic transfer function that operates in a time-domain, and wherein the dynamic transfer function is implemented using a first order low-pass filter.

14. The system of claim 13, wherein the processing circuitry is further configured to:
control charging of a power source of the medical device based on the estimated temperature of the external surface of the housing of the medical device.

15. The system of claim 14, wherein the processing circuitry is implemented by an external charging device.

16. The system of claim 13, wherein the dynamic transfer function is based on thermal properties of the housing of the medical device.

17. A non-transitory computer-readable storage medium having stored thereon instructions that, when executed, cause one or more processors to:
determine a temperature sensed by at least one temperature sensor of a first portion of a device;
determine, using an algorithm that incorporates the temperature of the first portion of the device, an estimated temperature of a second portion of the device, wherein the algorithm is representative of an estimated temperature difference between the first portion of the device and the second portion of the device according to at least a dynamic transfer function that operates in a time-domain, and wherein the dynamic transfer function is implemented using a low-pass filter; and
control a charging of the power source of the device based on the estimated temperature of the second portion of the device.

18. The non-transitory computer-readable storage medium of claim 17, wherein the low-pass filter includes a first order low-pass filter or a second or higher order low-pass filter.

19. A method comprising:
determining, via at least one temperature sensor, a temperature of a first portion of a device during a charging process of a power source of the device;
estimating, by processing circuitry and using an algorithm that incorporates the temperature of the first portion of the device, a temperature of a second portion of the device, wherein the algorithm is representative of an estimated temperature difference between the first portion of the device and the second portion of the device according to at least a dynamic transfer function that operates in a time-domain,
wherein the device includes a plurality of temperature sensors including the at least one temperature sensor, wherein estimating the temperature of the second portion of the device further comprises:
receiving a temperature value from each of the plurality of temperature sensors;
identifying, from the temperature values received from the plurality of temperature sensors, a temperature value that is greater than the other temperature values obtained via the plurality of temperature sensors; and
estimating, based on the dynamic transfer function, the temperature of at least one spot on the second portion of the device based at least in part on the temperature values received from each of the plurality of temperature sensors; and
controlling, by the processing circuitry and based on the temperature of the second portion of the device, charging of the power source, wherein controlling charging of the power source comprises:
determining a maximum temperature estimate based on the plurality of temperature sensors; and
determining a target charging power by at least utilizing a PID control algorithm that incorporates the maximum temperature estimated from the plurality of temperature sensors.

20. The method of claim 19, wherein a first temperature sensor of the plurality of temperature sensors corresponds to a first transfer function, and wherein a second temperature sensor of the plurality of temperature sensors corresponds to a second transfer function, wherein the first transfer function is different than the second transfer function.

* * * * *